United States Patent [19]

Yamamoto et al.

[11] Patent Number: 5,830,643
[45] Date of Patent: Nov. 3, 1998

[54] PARTIALLY DOUBLE-STRANDED OLIGONUCLEOTIDE AND METHOD FOR FORMING OLIGONUCLEOTIDE

[75] Inventors: Nobuko Yamamoto, Isehara; Kinya Kato, Yokohama; Harumi Iwashita; Masanori Sakuranaga, both of Atsugi, all of Japan

[73] Assignee: Canon Kabushiki Kaisha, Tokyo, Japan

[21] Appl. No.: 974,303

[22] Filed: Nov. 10, 1992

Related U.S. Application Data

[63] Continuation of Ser. No. 485,048, Feb. 26, 1990, abandoned.

[30] Foreign Application Priority Data

| Feb. 28, 1989 | [JP] | Japan | 1-48908 |
| Mar. 1, 1989 | [JP] | Japan | 1-50738 |
| Oct. 12, 1989 | [JP] | Japan | 1-266956 |
| Dec. 29, 1989 | [JP] | Japan | 1-343134 |
| Jan. 12, 1990 | [JP] | Japan | 2-3338 |
| Feb. 6, 1990 | [JP] | Japan | 2-27653 |
| Feb. 7, 1990 | [JP] | Japan | 2-29300 |

[51] Int. Cl.$^6$ .............................. C12Q 1/68; C12P 19/34; C07H 21/00
[52] U.S. Cl. .............................. 435/6; 435/91.2; 536/25.4
[58] Field of Search ....................... 435/6, 91.2; 536/25.4

[56] References Cited

U.S. PATENT DOCUMENTS

| 4,581,333 | 4/1986 | Kourilsky et al. | 435/6 |
| 4,605,735 | 8/1986 | Miyoshi et al. | 536/26.3 |
| 4,711,955 | 12/1987 | Ward et al. | 536/25.32 |
| 4,734,363 | 3/1988 | Dattagupta | 435/91.5 |
| 4,752,566 | 6/1988 | Collins et al. | 435/6 |
| 4,767,699 | 8/1988 | Vary et al. | 435/6 |
| 4,797,355 | 1/1989 | Stabinsky | 435/6 |
| 4,806,631 | 2/1989 | Carrico et al. | 536/27.12 |
| 4,963,602 | 10/1990 | Dattagupta | 435/6 |

FOREIGN PATENT DOCUMENTS

| 0097373 | 4/1984 | European Pat. Off. | 435/6 |
| 0196762 | 10/1986 | European Pat. Off. . | |
| 0246864 | 11/1987 | European Pat. Off. . | |
| 0297379 | 1/1989 | European Pat. Off. . | |

OTHER PUBLICATIONS

Abstract, Japanese Patent Application No. 63–117262, May 21, 1988.
Abstract, Japanese Patent Application No. 59–122499, Jul. 14, 1984.
Abstract, European Patent Application No. 0 168 342, Jan. 15, 1986.
Abstract, Japanese Patent Application No. 63–243875, Oct. 11, 1988.
Saiki, et al., Science, vol. 239, 481–491 (1988).
Tabor, et al., Proc. Natl. Acad. Sci.USA, vol. 84, pp. 4767–4771 (Jul. 1987).
Betsholtz, et al., Nature, vol. 320, pp. 695–699 (Apr. 1986).
Chollet, et al., Nucleic Acid Research, vol.13, No.5, pp.1529–1541 (1985).
Lauffer, et al., Nature, vol. 318, pp. 334–338 (Apr. 1986).
Rossi, et al., The Journal of Biological Chemistry, vol. 257, No. 16, pp. 9226–9229 (Aug. 25, 1962).
Matthews et al, Analytical Biochem, V. 169, pp. 1–25, Feb. 1988.
Venetianer et al Proc Natl Acad Sci 71(10) 3892–95 1974.
Feinberg et al Analytical Biochemistry 132:6–13(1983).
Rossi et al. Journal of Biological Chemistry 257:16 pp. 9226–9229 (1982).
Kharana Science 203:614–25 (1979).
Manning et al Biochemistry 16(7) 1364–70 (1977).

*Primary Examiner*—George C. Elliott
*Assistant Examiner*—Terry A. McKelvey
*Attorney, Agent, or Firm*—Fitzpatrick, Cella, Harper & Scinto

[57] ABSTRACT

A method for forming an oligonucleotide comprises the steps of synthesizing a pair of oligonucleotides, one oligonucleotide having a base sequence portion comlementary to that of the other at a part of the terminal end region thereof; binding the pair of oligonucleotides at the complementary base sequence portions; and polymerizing nucleic acid bases onto the resulting pair of oligonuceotides. The method may further comprise the step of separating the oligonucleotides thus obtained into single strands.

5 Claims, 4 Drawing Sheets

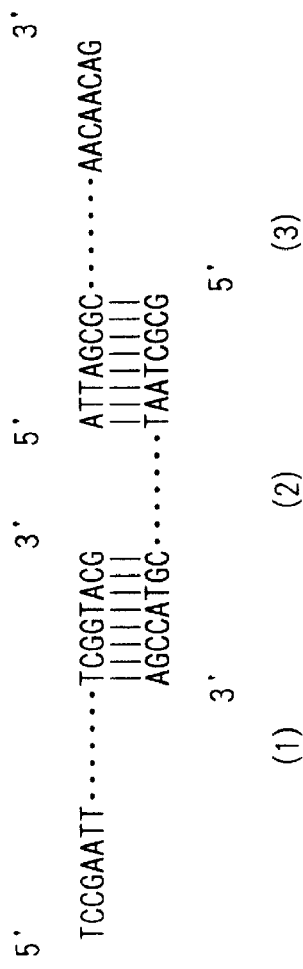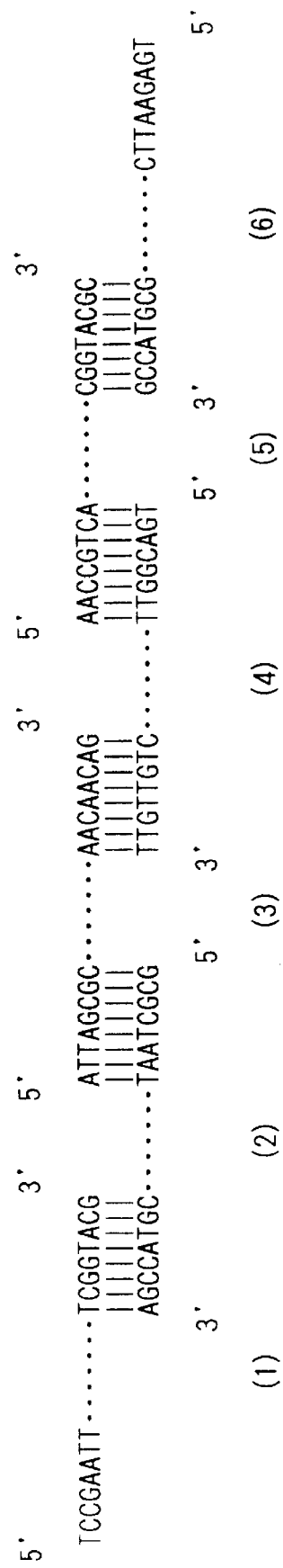
FIG. 2
FIG. 3

PARTIALLY DOUBLE-STRANDED OLIGONUCLEOTIDE AND METHOD FOR FORMING OLIGONUCLEOTIDE

This application is a continuation of application Ser. No. 07/485,048 filed Feb. 26, 1990, which is now abandoned.

BACKGROUND OF THE INVENTION

1. Field of the Invention

This invention relates to a novel method for forming a double-stranded oligonucleotide.

Also, the present invention relates to a formation method which can be suitably used for a method for forming a labelled double-stranded oligonucleotide.

Further, the present invention relates to a method for imparting a capturing function to an oligonucleotide. And, the present invention relates to a method for forming a nucleic acid probe for detection of presence of a nucleic acid sequence such as gene.

2. Related Background Art

Owing to the development in genetic manipulation technology in recent years, it has become possible to obtain a protein which is the genetic product in a large amount by cloning a specific gene and having that expressed in *E. coli*, *B. subtilis*, etc. According to this method, since the protein is produced in a microorganism of which growth is rapid, there is an advantage that even a protein which can be in itself purified and separated with difficulty by enzymes can be obtained easily and yet in a large amount, whereby the cost can be reduced in industry.

However, on the other hand, it does not necessarily follow that any protein can be well expressed by the same method. In such a case, there are many examples where expression has been rendered possible by replacing the base sequence of the structural gene of a desired protein with, for example, the codon well used in *E. coli* to constitute a synthetic gene.

Also, there have been recently made attempts to modify proteins for examination of the relationship of their functions with the amino acid sequences, or for making their functions higher. In such a case, it has been frequently practiced that a gene is constructed by introducing previously a restriction enzyme cleavage site as far as possible into the structural gene of the protein without changing the amino acid sequence, synthesizing and expressing it, followed by replacement of a part by utilizing the restriction enzyme cleavage site introduced to modify the protein.

Presently, among the synthetic methods of gene (hereinafter referred to as double-stranded oligonucleotide) practiced, for example, there is a method in which respective chains of the desired DNA are separated into 100 mers or less, which are synthesized by a DNA synthesizer and formed into a double strand by annealing, or after they are formed into double strands, ligated so as to be arranged consecutively. To describe specifically, when a double-stranded oligonucleotide of 100 base pairs is desired to be synthesized, two oligonucleotides of 100 mers are synthesized, then the oligonucleotides complementary to each other are mutually annealed to form a double strand, or when a double-strand of 200 base pairs is desired to be synthesized, 4 oligonucleotides of 100 mers are synthesized, and then the oligonucleotides complementary to each other are mutually annealed to form a double strand, followed by ligation of two sets of said double strands. When a gene of 500 base pairs is desired to be obtained, 10 oligonucleotides of 100 mers are synthesized, and then the oligonucleotides complementary to each other are mutually annealed to form double strands, followed by ligation successively, etc.

In preparing such a double-stranded oligonucleotide if its length is 100 mer or less, in place of forming two single-stranded oligonucleotides complementary to each other and forming a double strand by annealing, a primer can be synthesized and a double strand can be formed according to the primer extension method.

More specifically, in the case of synthesizing a double-stranded oligonucleotide of 100 base pairs, one oligonucleotide of 100 mers is synthesized, and by using it as a template, and also bonding it to an oligonucleotide of 8 bases or more having a sequence complementary to said oligonucleotide as the primer, nucleic acid bases can be polymerized successively from the primer side.

On the other hand, as the representative DNA labelling methods, there have been known those utilizing (1) the end labelling method, (2) the nick translation method, (3) the substitution synthetic method, and (4) the primer extension method.

In the following, the respective methods for obtaining labelled double-stranded oligonucleotide are described.

The end labelling method is a method in which the phosphoric acid group at the 5'-end of oligonucleotide is eliminated with alkali phosphatase, and a polynucleotide kinase is allowed to act thereon to label it when phosphorylating it again. The end labelling method is utilized for radioactive labelling with $^{32}$P. On the other hand, for labelling of the 3'-end, there are the terminal transferase method, the DNA polymerase method, etc. The terminal transferase method is a method in which a number of nucleotide triphosphates labelled with an enzyme are bonded successively at the 3'-end, while the DNA polymerase method is a method in which the protrudent single strand portion of the DNA cleaved with an restriction enzyme is modified, and the labelled nucleotide is incorporated during formation of a complementary double strand. Since in the end labelling method the site to be thus modified is limited to about one or two places, it is difficult to obtain a probe with high specific activity. Generally, labelling with radioisotope having high specific activity is performed.

In contrast, the nick translation method and the substitution synthetic method can prepare a DNA probe having high specific activity by incorporation of a large number of labelling compounds. In short, in the nick translation method, a double strand of DNA is hydrolyzed randomly with DNase I derived from pancreas to form nicks. DNA polymerase I recognizes the nicks and decomposes the DNA chain from the 5'-side, and at the same time a complementary DNA is synthesized with the DNA chain having no nick as the template by the polymerase activity in the direction from the 5'-side to the 3'-side, whereby the labelled nucleotide is incorporated as the substrate. On the other hand, the substitution synthetic method is a method in which the both 3'-ends of the double strand are cut in suitable lengths by 3'-exonuclease activity of T4 DNA polymerase, and then the labelled nucleotide is incorporated during modification by polymerase activity. Both of said methods are effective only when labelling long DNA of some hundred base pairs or more.

The primer extension method is a method in which there is utilized the Sanger method for determining the base sequence of DNA, and in which a single-stranded DNA oligonucleotide which becomes the template is synthesized, its 3'-end is bonded to an oligonucleotide of 8 bases or more having a complementary sequence as the primer, and the labelled nucleotide is incorporated during synthesis of DNA having a complementary sequence from the 5'-side to the 3'-side with a large fragment of DNA polymerase I, etc.

The synthesizing ability of a commercially available DNA synthesizer is presently about 100 mers or less. Besides, the yield cannot be said to be high. Accordingly, the oligonucleotide synthesized is separated by gel electrophoresis, etc. and the only desired band must be extracted. For example, in the case as described above (when synthesizing a double-stranded oligonucleotide of 200 base pairs), 4 oligonucleotides of 100 mers are synthesized, and further purified before use. Also, in the case of synthesizing a double-stranded oligonucleotide of 500 base pairs, 10 oligonucleotides of 100 mers are synthesized, and further purified before use.

Next, these oligonucleotides are annealed to form double strands, which are in turn ligated. In this case, and there are two kinds of oligonucleotides in respect of the binding order, the two sets of AB and BA. Therefore, for the bound products, by determining the base sequence, only the order of AB is required to be selected. Necessarily, two kinds of bound products are obtained in the both directions, and the operation for obtaining only the desired product by determining the base sequences thereof is required. However, the above operation is considerably complicated, and yet when purification is performed for satisfying the purity, the synthesis yield becomes poor. Thus, this method was not satisfactory in both purity and yield.

Also, as described above, even if a double-stranded oligonucleotide may be formed by the primer extension method, etc., the maximum number of base pairs of the double-stranded oligonucleotide before ligation by annealing is up to 100 (because the synthesis ability of single-stranded oligonucleotide is presently 100 mers or less), and there has not been obtained a method of synthesizing a double-stranded oligonucleotide of 200 base pairs at once without the operation of ligation.

On the other hand, generally speaking, as the length of the DNA oligonucleotide utilized as the probe is longer, the error of complementary bonding during hybridization can be prevented. However, for obtaining a long labelled DNA according to the primer extension method, a long single-stranded DNA is required which becomes the template. Whereas, the synthesis yield by a DNA synthesizer is lowered, as the length of the oligonucleotide to be synthesized is longer. Besides, also the by-products with shorter chain lengths are increased, and therefore the desired product is required to be purified by separation in order to utilize it as the template DNA.

Also, in the case of synthesizing a long region with DNA polymerase, synthesis may be sometimes stopped in the course by some obstacle, thereby giving rise to difference in length of the labelled oligonucleotides. Particularly, when a non-radioactive labelling substance is to be incorporated, the side chain of the labelling substance, etc. interferes with the enzyme reaction, whereby products with shorter lengths than those expected previously are liable to be formed. This not merely lowers the efficiency of hybridization, but also affects the reaction conditions of hybridization (temperature, formamide content, etc.), and may probably result in unsuccessful hybridization reaction itself.

Further, according to this method, one chain of the double strand functions only as the template, and the chain which is labelled and functions as the probe in the hybridization reaction mixture is only one on the primer side. Therefore, it follows that only half of all DNAs is utilized, whereby efficiency is poor. Further, during the hybridization reaction, the unlabelled template DNA may antagonize the labelled probe, whereby there is the possibility that the detection sensitivity may be lowered.

This problem applies to all the probes synthesized by the primer extension method irrespectively of the length of the probe, and a large amount of probes is required in a system where high sensitivity is demanded, and further in some cases, the operation of recovering only the template portion having no label may be required.

Also, during ligation by annealing, the annealed portion is stable as it is longer, but in the case of a short probe to be used for detection of genetic disease, etc., the ratio of the annealed portion based on the whole is increased and the labelled portion is decreased, whereby specific activity as the probe is lowered.

On the other hand, in the hybridization reaction, a labelled oligonucleotide or polynucleotide, namely a probe can form a base pair with the target nucleic acid.

There has been known a method in which a hybrid is formed with the target nucleic acid after fixing on a carrier having the function capable of separating the probe nucleic acid from the unreacted material, and then the hybrid is separated by the centrifugation method. As an example, there is Japanese Patent Application Laid-Open No. 63-117262, etc. More specifically, according to these methods, first a nucleic acid under the state of a single strand containing the base sequence complementary to a specific base sequence of the target is bound to the surface of particles comprising an organic polymer substance with nonporous surfaces having particle sizes of 0.01 to 50 $\mu$m, to form a probe nucleic acid for formation of hybrid bound to a carrier having the function capable of being separated from the unreacted material. Next, the probe nucleic acid is reacted with the sample to form a hybrid with the target nucleic acid containing the specific base sequence. By eliminating the nucleic acid having formed no hybrid with the probe nucleic acid on the carrier and other intervening matters by the centrifugation method, etc., the target nucleic acid forming the hybrid is detected. Otherwise, as the method for separating or fixing the material to be detected, there have been known the following two methods.

One method is (1) to modify chemically the 5'- or 3'-end of a probe nucleic acid, and a specific example is to bind a substance for capturing an insoluble carrier to the 3'-end side of the probe nucleic acid by use of Terminal Deoxynuceltidyl Transferase as shown in Japanese Patent Application Laid-Open No. 63-243875.

The second method is (2) to fix a nucleic acid as a whole by use of an organic solvent. This is described in detail in, for example, Japanese Patent Application Laid-Open No. 59-122499.

In the hybridization reaction, first of all, the reaction is carried out at a constant temperature so that the probe and the target DNA may form a hybrid through hydrogen bonds. Here, if the temperature is too high, the probe and the DNA having the complementary sequence cannot be bonded, while if it is too low, the probe will be bound non-specifically to the DNA. Also, if formamide is added into the reaction mixture, interference with formation of nonspecific hybrid occurs.

Next, after the hybridization reaction, by lowering the salt concentration in the solution or elevating the temperature of the solution, the probe non-specifically bound is washed away. By these operations, only the DNA fragment having the sequence complementary to the probe can be detected.

In the case of a long probe (1000 base pairs), these conditions are substantially established, but setting of conditions in the case of using a synthetic oligonucleotide is considerably difficult. Presently, those of 30 mers or less are frequently utilized as the oligonucleotide probe, but in the case of such short probes, the reaction conditions of hybridization are made moderate so that it may surely form the hybrid with the desired DNA. In other words, setting of conditions such as lowering of temperature or reducing the content of formaldehyde, etc. are required. Also, for washing after the reaction, the conditions must be selected for eliminating the non-specific bonds of the probe without destroying hybrid formation in itself, but trials and errors are necessary for setting of such conditions.

For solving this problem, there has been frequently employed a method in which two kinds of oligonucleotide probes are prepared, screening is performed with the first probe, and thereafter screening is performed again with the second probe. However, this method requires much care and is time consuming.

Rather than such method, it is preferable to use a longer probe and remove completely the non-specific hybrids by making the conditions of hybridization and the conditions of washing more strict.

In other words, as the length of the DNA oligonucleotide to be utilized as the capturing probe is longer, an error in complementary binding during hybridization can be prevented. However, in the two methods of the prior art (the methods (1) and (2) as described above), the necessary DNA as a whole is required to be synthesized in both cases.

On the other hand, there is the problem at the synthesis yield by means of a DNA synthesizer is lowered as the oligonucleotide to be synthesized is longer. In addition, the method of bonding by application of chemical modification at the 5'- or 3'-end has the following problems.

Since the site to be modified is limited to about 1 or 2 places, sufficient fixation can be obtained with difficulty, and it is difficult to obtain a probe with high capturing ability.

Also, in the case of a long nucleic acid for capturing, the probability of existence of the complementary sequence in the nucleic acid is enhanced, and it forms itself a higher structure during the hybridization reaction, playing no longer the function of capturing, whereby the effect of hybrid formation is markedly reduced.

In the method of carrying the nucleic acid as a whole by use of an organic solvent, although it can be avoided that the nucleic acid for capturing itself takes a higher structure as described above, it will take unpractically a long time for searching for the conditions of fixing the nucleic acid without changing the characteristics of the nucleic acid as a whole.

SUMMARY OF THE INVENTION

Accordingly, an object of the present invention is to provide a method which can form simply a double-stranded oligonucleotide, with good precision as well as high synthesis yield.

Another object of the present invention is to provide a method for forming a labelled double-stranded oligonucleotide having any desired length with good precision and high synthesis yield, and which can further form a labelled double-stranded oligonucleotide functioning as a probe with high specific activity.

Also, still another object of the present invention is to provide a method for preparing an oligonucleotide to be used as the probe for capturing which solves of such drawbacks of the prior art and said oligonucleotide.

In short, the present invention provides a method for forming an oligonucleotide, comprising:
  a) the step of synthesizing a pair of oligonucleotides, one oligonucleotide having a base sequence portion complementary to that of the other at a part of the terminal end region thereof,
  b) the step of binding the pair of oligonucleotides at the complementary base sequence portions; and
  c) the step of polymerizing nucleic acid bases onto the resulting pair of oligonucleotides.

There is also provided a method for forming a labelled oligonucleotide, comprising:
  d) the step of synthesizing at least a pair of oligonucleotides, one oligonucleotide having a base sequence portion complementary to that of the other at a part of the terminal end region thereof;
  e) the step of binding the pair of oligonucleotides at the complementary base sequence portions; and
  f) the step of polymerizing nucleic acid bases including a labelled nucleic acid base onto the resulting pair of oligonucleotide.

There is also provided a partially double-stranded oligonucleotide having parts of the terminal end regions of the respective oligonucleotides bound through complementary sequences, and having parts of the respective non-binding portions.

There is also provided a method for forming an oligonucleotide comprising:
  (1) the step of synthesizing a first oligonucleotide and a second oligonucleotide having base sequence portions complementary to each other at the respective 3'-end regions, and the step of synthesizing a third oligonucleotide having a 5'-end region having a base sequence portion complementary to the 5'-end regions of the first and second oligonucleotides,
  (2) the step of binding said first oligonucleotide and second oligonucleotide at the complementary base sequence portions, and the step of binding either of the first oligonucleotide or second oligonucleotide to the third oligonucleotide at said complementary base sequence portions; and
  (3) the step of polymerizing and ligating nucleic acid bases onto the oligonucleotide obtained via the above steps (1) and (2).

There is also provided a method for forming a labelled oligonucleotide, comprising:
  (4) the step of synthesizing a first oligonucleotide and a second oligonucleotide having base sequence portions complementary to each other at the respective 3'-end regions, and the step of synthesizing a third oligonucleotide having a 5'-end region having a base sequence portion complementary to the 5'-end regions of the first and second oligonucleotides;
  (5) the step of binding the first oligonucleotide and second oligonucleotide at the complementary base sequence portions, and the step of binding either of the first oligonucleotide or second oligonucleotide to the third oligonucleotide at the complementary base sequence portions; and
  (6) the step of polymerizing and ligating nucleic acid bases including labelled nucleic acid bases onto the resulting oligonucleotides obtained via the above steps (4) and (5).

There is also provided a method for forming a nucleic acid probe, comprising:

(4) the step of synthesizing a first oligonucleotide and a second oligonucleotide having base sequence portions complementary to each other at the respective 3'-end regions, and the step of synthesizing a third oligonucleotide having a 5'-end region having a base sequence portion complementary to the 5'-end regions of the first and second oligonucleotides, (5) the step of binding said first oligonucleotide and second oligonucleotide at the complementary base sequence portions, and the step of binding either of said first oligonucleotide or second oligonucleotide to the third oligonucleotide at the complementary base sequence portions;

(6) the step of polymerizing and ligating nucleic acid bases including labelled nucleic acid bases onto the resulting oligonucleotide obtained via the above steps (4) and (5), and further (7) the step of separating the labelled oligonucleotide obtained via the step of (6) into single strands.

There is also provided a partially double-stranded oligonucleotide comprising at least three oligonucleotides, wherein the respective 3'- and 5'-end regions of said each oligonucleotide are complementary to the 5'- and 3'-end regions of said other two oligonucleotide, both of the terminal regions of said partially double-stranded oligonucleotide being non-binding.

There is also provided a method for forming an oligonucleotide comprising:

d) the step of synthesizing a pair of oligonucleotides, one oligonucleotide having a base sequence portion complementary to that of the other at a part of the terminal end region thereof;

e) the step of bonding the pair of oligonucleotides at the complementary base sequences; and h) the step of polymerizing nucleic acid bases, any of which has a fixing substance specifically reactive with a carrier, onto the resulting pair of the oligonucleotides.

There is also provided a method for forming a nucleic acid probe, comprising:

d) the step of synthesizing a pair of oligonucleotides, one oligonucleotide having a base sequence portion complementary to that of the other at a part of the terminal end region thereof;

e) the step of binding said pair of oligonucleotides as the complementary base sequences;

h) the step of polymerizing nucleic acid bases, any of which has a fixing substance specifically reactive with a carrier, onto the resulting pair of the oligonucleotides, and further, i) the step of separating the oligonucleotides obtained via the step of h) into single strands.

There is also provided a method for forming an oligonucleotide, comprising:

(4) the step of synthesizing a first oligonucleotide and a second oligonucleotide having base sequence portions complementary to each other at the respective 3'-end regions, and the step of synthesizing a third oligonucleotide having a 5'-end region having a base sequence portion complementary to the 5'-end regions of the first and second oligonucleotides;

(5) the step of binding the first oligonucleotide and second oligonucleotide at the complementary base sequence portions, and the step of binding either of the first oligonucleotide or second oligonucleotide to the third oligonucleotide at the complementary base sequence portions;

(8) the step of polymerizing nucleic acid bases, any of which has a fixing substance specifically reactive with a carrier, onto the resulting oligonucleotides obtained via the above steps (4) and (5).

There is also provided a method for forming an oligonucleotide comprising:

j) the step of synthesizing at least a pair of oligonucleotides, one oligonucleotide having a base sequence portion complementary to that of the other at a part of the terminal end region thereof, and the complementary base sequence portions having 13 or more hydrogen bonds formed between one oligonucleotide and the other oligonucleotide;

k) the step of binding the pair of oligonucleotides at the complementary base sequence portions; and l) the step of polymerizing nucleic acid bases onto the resulting pair of oligonucleotides.

There is also provided a method for forming a nucleic acid probe, comprising:

j) the step of synthesizing at least a pair of oligonucleotides, one oligonucleotide having a base sequence portion complementary to that of the other at a part of the terminal end region thereof, and the complementary base sequence portions having 13 or more hydrogen bonds formed between one oligonucleotide and the other oligonucleotide;

k) the step of binding the pair of oligonucleotides at the complementary base sequence portions;

l) the step of polymerizing nucleic acid bases onto the resulting pair of oligonucleotides, and further m) the step of separating the double-stranded oligonucleotide obtained via the step 1) into single strands.

There is also provided a partially double-stranded oligonucleotide having parts of the terminal end regions of the respective oligonucleotides bound through complementary sequences, and the total hydrogen bond number of bases at the complementary portions being 13 or more, and having parts of respective non-binding portions.

There is also provided a method for forming an oligonucleotide comprising:

(10) the step of synthesizing a first oligonucleotide and a second oligonucleotide having base sequence portions complementary to each other at the respective 3'-end regions, and the step of synthesizing a third oligonucleotide having a 5'-end region having a base sequence portion complementary to the 5'-end regions of the first and second oligonucleotides;

(11) the step of binding the first oligonucleotide and second oligonucleotide at the complementary base sequence portions, and the step of binding either of the first oligonucleotide or second oligonucleotide to the third oligonucleotide at the complementary base sequence portions; and

(12) the step of polymerizing and ligating nucleic acid bases having labelled nucleic acid bases onto the oligonucleotide obtained via the above steps (10) and (11), wherein in the above step (10), the complementary base sequence portions at the 3'-end and the 5'-end have 13 or more hydrogen bonds formed between one oligonucleotide and the other oligonucleotide.

There is also provided a method for forming a nucleic acid probe comprising:

(10) the step of synthesizing a first oligonucleotide and a second oligonucleotide having base sequence portions complementary to each other at the respective 3'-end regions, and the step of synthesizing a third oligonucleotide having a 5'-end region having a base sequence portion complementary to the 5'-end regions of the first and second oligonucleotides;

(11) the step of binding the first oligonucleotide and second oligonucleotide at the complementary base sequence portions, and the step of binding either of the first oligonucleotide or second oligonucleotide to the third oligonucleotide at the complementary base sequence portions;

(12) the step of polymerizing and ligating nucleic acid bases having labelled nucleic acid bases with the oligonucleotide obtained via the above steps (10) and (11);

(13) the step of separating the double-stranded oligonucleotide obtained via the above step (12) into single strands, wherein in the above step (10), the complementary base sequence portions at the 3'-end and the 5'-end have 13 or more hydrogen bonds formed between one oligonucleotide and the other oligonucleotide.

There is also provided a partially double stranded oligonucleotide comprising at least three oligonucleotides, wherein the respective 3'- and 5'-end regions of said each oligonucleotide are complementary to the 5'- and 3'-end regions of said the other two oligonucleotide, both of the terminal regions of said partially double-stranded oligonucleotide are non-binding, and the total hydrogen bond number at the bases of the complementary sequence portions of said 3'-ends and 5'-ends is 13 or more.

BRIEF DESCRIPTION OF THE DRAWINGS

FIG. 1, FIG. 2 and FIG. 3 are schematic diagrams for illustration of the partial double strands to be used in the present invention.

DETAILED DESCRIPTION OF THE PREFERRED EMBODIMENTS

Figure 1:
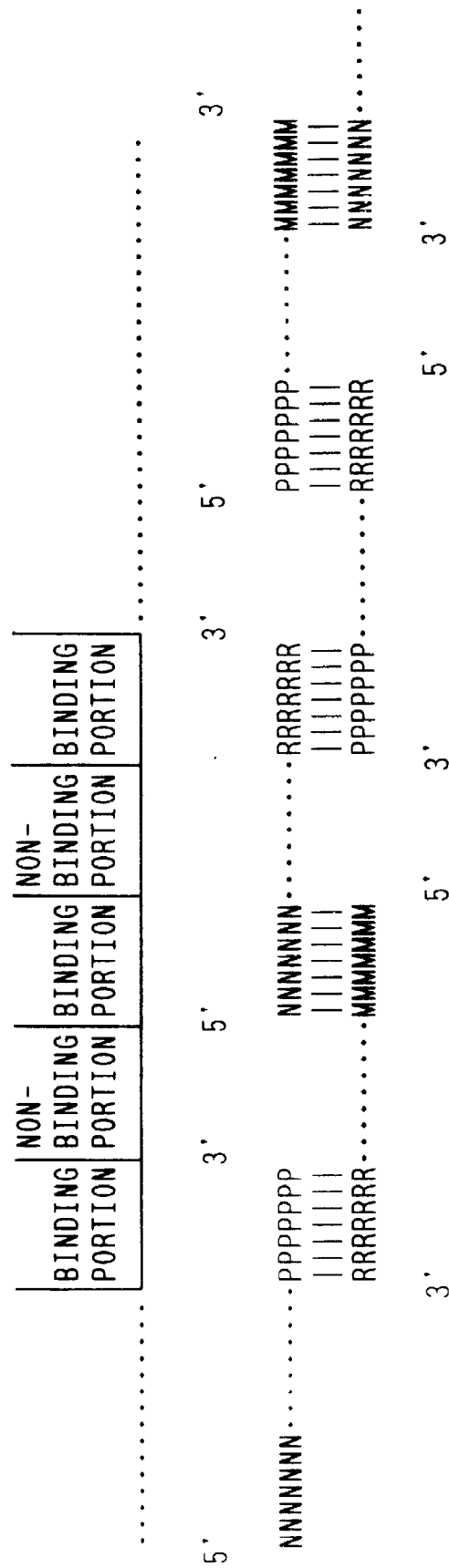

The first present invention has been achieved so that each chain of the double strand may function as both a template and a primer for oligonucleotide polymerization by improvement of the primer extension method of the prior art.

The template and the primer in the first invention, when two kinds of oligonucleotides synthesized form a partial double strand with complementary sequences, refer to the protrudent single strand which is the non-binding portion as the template, while of the respective chains constituting the partial double strand, the chain participating in binding on the opposite side to the protrudent single strand is referred to as the primer.

In short, the present invention may be specifically described as follows.

(a) Two single-stranded oligonucleotides with complementary sequences at the 3'-ends are synthesized by a DNA synthesizer. (b) Next, these two oligonucleotides are bound at the complementary sequences by the annealing reaction to form partially a double strand. (c) The partial double strand formed at this time functions as the primer of the DNA's synthesized respectively. With different nucleotide triphosphates and reagents for polymerization of the nucleotide triphosphates, a double-strand is formed while synthesizing oligonucleotides having complementary sequences in the direction from the 5'-side to the 3'-side with the protrudent single strand as the template.

To describe in more detail, the length of the oligonucleotide synthesized in (a) may be shorter than that practically required. The total hydrogen bond number in the complementary region when a pair of oligonucleotides are formed may be preferably 16 to 24, but may be shorter than that, provided that it is 13 or more, more preferably 16 or more, or may be even longer.

(b) In the annealing reaction, the mixture of the two kinds of single-stranded oligonucleotides is heated in an appropriate buffer at 65° C. or higher for one minute or longer, preferably at 65° C. for 10 minutes, or at 95° C. for one minute or longer, and then the solution is left to cool to room temperature. According to this reaction, the oligonucleotides are bound at the sequences complementary to each other to form a partial double-strand.

(c) Into the solution are added appropriate amounts of dATP, dCTP, dGTP, and TTP as synthetic reagents which are nucleotide triphosphates.

Also, for the enzyme to be used as the polymerizing reagent, there may be employed E. coli DNA polymerase I, Klenow fragment of DNA polymerase, T4DNA polymerase (T. Maniatis et al, Molecular Cloning 108, Cold Spring Harbar Laboratory), T7DNA polymerase (S. Tabor et al, Proc. Natl. Acad. Sci. USA, 84, 4767–4771 (1987), thermally stable DNA polymerase (R. k. Saiki et al, Science, 239, 487–491 (1988), other available DNA polymerases, reverse transcriptases, and other enzymes, such as enzymes promoting binding of nucleotides in appropriate modes for forming the primer extension products of the respective nucleic acids which are complementary.

The polymerization reaction may be performed at the temperature where any of the above-mentioned polymerizing reagent can function without cleavage of the hydrogen bonds at the annealed portion. For example, a system wherein polymerization reaction is carried out at 0° to 40° C. by use of Klenow fragment of DNA polymerase is preferred.

As described above, a double-stranded oligonucleotide is formed via a partial double-stranded oligonucleotide.

On the other hand, a labelled double-stranded oligonucleotide can also be formed by utilizing the method as described above and as described similarly below.

In short, (d) two single-stranded oligonucleotides having sequences complementary to each other at the 3'-ends are synthesized by a DNA synthesizer. (e) Next, these two oligonucleotides are bound at the complementary portions by the annealing reaction to constitute partially a double strand. (f) The partial double-strand formed at this time functions as the primer of the DNA's synthesized respectively, and with different nucleotide triphosphates, a labelled nucleotide triphosphate, and the reagents for polymerization of the nucleotide triphosphates, and with the protrudent single-stranded portions as the templates, a double strand is formed while synthesizing oligonucleotides having sequences complementary to each other in the direction from the 5'-side to the 3'-side. During the reaction, the labelled nucleotide triphosphate can be incorporated. The product of the reaction is treated under denaturation conditions, and used as the probe for hybridization reaction. (d), (e) are the same as (a), (b) as described above. Now, (f) is to be described in more detail.

(f) Into said solution are added dATP, dCTP, dGTP, and TTP as synthetic reagents, which are nucleotide triphosphates, in appropriate amounts. Here, one or more kinds of labelled nucleotide phosphates are added. In this case, the only labelled substance may be added, or unlabelled substances may be permitted to exist as a mixture. As the labelling substance, radioisotopes as a matter of course, and non-radioactive labelling substances, typically biotin or dinitrophenylnucleotide derivative, can be used. The enzymes to be used as the polymerization reagent are as described above.

By forming a double-stranded oligonucleotide according to the formation method as described above, a double-stranded oligonucleotide comprising oligonucleotides with a length of 100 mer or more can be simply prepared.

1) According to the primer extension method of the prior art, it has been difficult to prepare a nucleotide oligomer of about 100 mer at once with good precision and with good yield. This is because, for the purpose, synthesis of a template DNA having such length is required, and also the synthesis of the DNA synthesizer is limited to about 100 mer. Besides, when 100 mer is attempted to be synthesized, the synthesis yield is 10% or lower under the present situation. Therefore, only those with desired lengths are required to be purified to remove by-products before the next reaction. However, it is very difficult to purify with good precision without an error of single base.

In contrast, in the method of the present invention, it is satisfactory to synthesize oligonucleotides with lengths shorter than the length of the probe. Accordingly, when a gene of 100 base pairs is to be prepared, if the annealing portion is made 8 base pairs, for example, two oligonucleotides with a length of 54 bases may be synthesized. As a matter of course, as compared with the case of synthesizing an oligonucleotide with 100 bases, the case of 54 bases has better synthesis efficiency and also less by-products. Therefore, purification is also simple.

Further, according to the present invention, it becomes possible to synthesize a gene of 100 mer or more, for example, to synthesize a gene of 200 base pairs, etc. at once, which has been almost impossible in the prior art. By synthesizing two oligonucleotides of 100 mer where 100 mer is the limit that can be synthesized at once in a synthesizer, and performing the extension reaction with enzymes, a gene with a length approximate to 200 base pairs can be synthesized.

2) Also in the reaction with polymerization reagents, in the case of the prior art method, a large number of nucleotides must be polymerized with enzymes. Whereas, the lengths which can be extended with enzymes are also limited. As the result, the reaction is stopped in the course, whereby shorter genes are easily formed.

In the case of the present invention, the length of the nucleotide polymerized with an enzyme is considerably shorter than in the prior art. In the case of preparing a gene of 100 mer, 92 bases are extended in the prior art method, while in the present invention 46 bases are satisfactory to be extended. As compared with extension of 92 bases, the case of extending 46 bases can proceed within a short time and more completely. For this reason, a double-stranded DNA with uniform lengths can be obtained, whereby ligation reaction efficiency to vector, and transformation efficiency are improved to a greater extent.

Further, when the double-stranded oligonucleotide is labelled by use of the method of the present invention, there are the following advantages.

3) In the reaction with polymerizing reagents, in the case of the prior art method, a large number of nucleotides must be polymerized with enzymes. Whereas, the lengths which can be extended with enzymes are also limited. Even in the case of labelling by use of a radioisotope, when the enzyme reaction product is examined by gel electrophoresis, many by-products with shorter bands than the desired band are observed. Therefore, in the case of the prior art method, only DNA with desired length must be cut out from the gel, and DNA must be extracted therefrom for use as the probe. In the case of a non-radioactive label, the structure of the labelling substance interferes with the enzyme reaction, consequently resulting in intermission of the reaction. Besides, as different from radioisotope label, since color formation reaction, etc. is utilized for detection, no purification by gel electrophoresis is possible. Then purification can be done with difficulty.

In the case of the present invention, the length of the nucleotide polymerized with an enzyme is considerably shorter than in the prior art. In the case of preparing a probe of 50 mer, 42 bases are extended in the prior art method, while in the present invention 21 bases is satisfactory to be extended. As compared with extension of 42 bases, the case of extending 21 bases can proceed in a shorter time and more completely, whereby no purification is required. For this reason, not only purification can be omitted, but also it becomes possible to obtain easily a labelled oligonucleotide with uniform lengths. In the present invention, further as the step (g), the oligonucleotide obtained in the above (f) is separated into single strands, and the oligonucleotides thus obtained are utilized as the probe. The probe obtained by this method makes it possible to prepare a probe with any desired length and with any desired number of labelled substances incorporated therein, whereby it becomes possible to prepare also a probe easily of 50 to 200 base pairs length, which was low in the ratio of label and could be prepared with difficulty according to the primer extension method or the nick translation method in the prior art.

Also, the double strand of the oligonucleotide obtained in the above step (f) has labelled substances incorporated in the both chains, and each chain functions as a probe with high specific activity, thereby enhancing the efficiency of hybridization.

As the result, elevation of sensitivity is observed also in analysis by use of a probe of 20 base pairs or lower which is effective for examination of presence of a specific sequence associated with genetic diseases, a tumor diseases or infectious diseases, or presence of repeated sequence.

The second present invention has been achieved so that each chain of a plurality of oligonucleotides may function as both of a template and a primer by improvement of the primer extension method of the prior art.

The template and the primer in the second invention, when plural kinds of oligonucleotides synthesized form a partial double strand with complementary sequences, refer to the protrudent single strand which is the non-binding portion as the template, while of the respective chains constituting the partial double strand, the chain participating in bonding on the opposite side to the protrudent single strand is referred to as the primer.

In short, the present invention may be specifically described as follows.

For a desired nucleic acid base sequence, (1) as shown in FIG. 1, a plural number of single-stranded oligonucleotides having complementary sequences at the 3'-end or the 5'-end are synthesized by a DNA synthesizer. (2) Next, phosphoric acid groups are attached at the 5'-ends of the respective oligonucleotides. (3) Next, these two oligonucleotides are bound at the complementary sequences by the annealing reaction to form partially a double strand. (4) One of the partial double strands formed here functions as the primer for the other oligonucleotide synthesized. With different nucleotide triphosphates and reagents for polymerization of the nucleotide triphosphates, a double strand is formed while synthesizing oligonucleotides having complementary sequences in the direction from the 5'-side to the 3'-side with the protruded single strand portion as the template. (5) When there is a nick formed in the oligonucleotide thus prepared, ligation may be performed with an enzyme so that there may be no nick.

To describe in more detail, the length of the oligonucleotide synthesized in (1) is the length which can be synthesized at once in a DNA synthesizer (generally 100 mer or less). The total hydrogen bond number in the complementary region when a pair of oligonucleotides are formed may be preferably 16 to 24, but may be shorter than that, provided that it is 13 or more, more preferably 16 or more, or may be even longer.

(2) The method for attaching phosphoric acid group to the 5'-end may be either by way of chemical synthesis or by use of an enzyme such as T4 polynucleotide kinase, etc. in the presence of ATP.

At least by attachment of phosphoric acid at the end of the oligonucleotide according to the operation, when the nucleic acid bases are polymerized in the above step (4), depending on selection of the polymerization reagent, ligation may be sometimes performed between the nucleic acid base naturally polymerized during polymerization and the end portion of the oligonucleotide attached with phosphoric acid group. However, when ligation is insufficient with such operation, ligation is performed by use of a ligating reagent as described below in (5).

(3) In the annealing reaction, the mixture of the plural kinds of single-stranded oligonucleotides is heated in an appropriate buffer at 65° C. or higher for one minute or longer, preferably at 65° C. for 10 minutes, or at 95° C. for one minute or longer, and then the solution is left to cool to room temperature. According to this reaction, the oligonucleotides are bound at the sequences complementary to each other to form a partial double strand.

(4) Into the solution are added appropriate amounts of dATP, dCTP, dGTP, and TTP as synthetic reagents, which are nucleotide triphosphates.

Also, for the enzyme to be used as the polymerizing reagent, E. coli DNA polymerase I, Klenow fragment of DNA polymerase, T4DNA polymerase (T. Maniatis et al, Molecular Cloning 108, Cold Spring Harbar Laboratory), T7DNA polymerase (S. Tabor et al, Proc. Natl. Acad. Sci. USA, 84, 4767–4771 (1987), thermally stable DNA polymerase (R. k. Saiki et al, Science, 239, 487–491 (1988), other available DNA polymerases, reverse transcriptases, and other enzymes, such as enzymes promoting binding of nucleotides in appropriate modes for forming the primer extension products of the respective nucleic acids which are complementary.

The polymerization reaction may be performed at the a temperature where any of the above-mentioned polymerizing reagent can function without cleavage of the hydrogen bonds at the annealed portion. For example, a preferred system is such that polymerization reaction is carried out at 0° to 40° C. by use of Klenow fragment of DNA polymerase.

The reaction of (5) is carried out with a DNA ligase. DNA ligase may be either one derived from E. coli or one derived from phage T4, or alternatively another enzyme which can function similarly.

As described above, a double-stranded oligonucleotide is formed via a partial double-stranded oligonucleotide.

On the other hand, a labelled double-stranded oligonucleotide can be also formed by utilizing the above method, as described similarly below.

(6) As shown in FIG. 1, a plural number of single-stranded oligonucleotides having complementary sequences at the 3'-end or 5'-end are synthesized by a DNA synthesizer. (7) Next, phosphoric acid groups are attached to the 5'-ends of the respective oligonucleotides. (8) Next, these two oligonucleotides are bound at the complementary portions by the annealing reaction to constitute partially a double strand. (9) The partial double strand formed at this time functions as the primer of the DNA's synthesized respectively, and with different nucleotide triphosphates, a labelled nucleotide triphosphate, and the reagents for polymerization of the nucleotide triphosphates, and with the protrudent single-stranded portions as the templates, a double strand is formed while synthesizing oligonucleotides having sequences complementary to each other in the direction from the 5'-side to the 3'-side. During the reaction, the labelled nucleotide triphosphate can be incorporated. (10) When there is a nick formed in the oligonucleotide thus prepared, ligation may be performed with an enzyme, etc. so that there may be no nick. As described above, a labelled double-stranded oligonucleotide is formed. Further, when hybridization reaction is used, (11) the product of the reaction is treated under the conditions to separate the double strand into single strands, and used as the probe for hybridization reaction. To describe in more detail, (6), (7) and (8) are the same as (1), (2) and (3) as described above.

Now, (9) is to be described in more detail.

(9) Into the solution added are appropriate amounts of dATP, dCTP, dGTP, and TTP as synthetic reagents, which are nucleotide triphosphates. At this time, one or more kinds of labelled nucleotide phosphates are added. In this case, only the labelled substance may be added, or unlabelled substances may be permitted to exist as a mixture.

When only labelled substance is added without addition of non-labelled nucleotide triphosphate at all, the DNA prepared becomes to be constituted of labelled regions and non-labelled regions alternately.

As the labelling substance, radioisotopes as a matter of course, and non-radioactive labelling substances, typically biotin or dinitrophenylnucleotide derivative, can be used. The enzymes to be used as the polymerization reagent are as described above.

The enzyme to be used as the polymerizing reagent may include E. coli DNA polymerase I, Klenow fragment of DNA polymerase, T4DNA polymerase (T. Maniatis et al, Molecular Cloning 108, Cold Spring Harbor Laboratory), T7DNA polymerase (S. Tabor et al, Proc. Natl. Acad. Sci. USA, 84, 4767–4771 (1987), thermally stable DNA polymerase (R. k. Saiki et al, Science, 239, 487–491 (1988), other available DNA polymerases, reverse transcriptases, and other enzymes, such as enzymes promoting binding of nucleotides in appropriate modes for forming the primer extension products of the respective nucleic acids which are complementary.

(10) A representative of the enzyme to be used as the ligating reagent is DNA ligase. DNA ligase may be either one derived from E. coli or one derived from phage T4, or alternatively another enzyme having similar function.

(11) Denaturation may be either by thermal denaturation (e.g. at 95° C. for 5 minutes), by the method with an alkali or another method which separates double-strand into single strands.

For example, when a double-stranded oligonucleotide with a length of 500 base pairs is desired to be prepared, according to the method of the prior art, it is necessary to synthesize 10 oligonucleotides of 100 mer and ligate them to one another.

In the case of preparing a long DNA by successive ligation of double-strands successively synthesized, for identification of the directionality during ligation, purifications in the respective ligation steps are required. Then the final yield will be lowered.

In contrast, in the formation method of the present invention as described above, the chain length is extended in the extension reaction after formation of the hydrogen bonds previously at the complementary sequences. There is the advantage that the reaction can be carried out all at once by use of a mixture of all the oligonucleotides.

Further, the method is improved in yield to great precision without purification.

When a gene of 500 base pairs is to be prepared by use of the formation method of the present invention (that is, when the portion of annealing is made 8 base pairs, for example, a double-stranded oligonucleotide is formed by synthesizing 5 oligonucleotides with a length of 100 mer and one oligonucleotide of 40 mer), as compared with 10 oligonucleotides of the prior art, the number of oligonucleotides can be half. Then reagents and time can be saved.

Further, as compared with the prior art, treatments in successive ligations and checking at the respective steps can be omitted.

Also, when a double-stranded oligonucleotide with a length of 100 base pairs is attempted to be formed according to the successive ligation method, preparing 4 oligonucleotides of 50 mer, there is the problem of low yield because of the directionality undetermined during ligation. Accordingly, it may be preferable to use a method to prepare two oligonucleotides of 100 mer at once, and form a double strand by annealing.

However, the method has also the following problem. When an oligonucleotide of 100 mer is tried to be synthesized at once, the synthesis yield is 10% or less under the present situation. Accordingly, it is necessary to purify only those with desired lengths to remove by-products before the next reaction, but it is very difficult to purify the product with good precision without an error of single base.

In contrast, by use of the method of the present invention, a double-stranded oligonucleotide can be synthesized by ligating the oligonucleotides with shorter lengths without the problem of low yield, etc. as explained in the successive ligation method as described above. For example, a double-stranded oligonucleotide with a length of 100 base pairs is formed according to the method of the present invention, for example, 4 oligonucleotides with a length of 25 mer and one oligonucleotide with a length of 24 mer may be synthesized by designing the annealing portion of 6 base pairs.

In short, it can not only overcome a problem of directionality during ligation in the successive ligation method as described above, but also synthesis efficiency is better in synthesis of an oligonucleotide of 25 mer than in synthesis of an oligonucleotide of 100 mer, with the by-products being also less. Therefore, purification becomes also simpler.

Further, in the case where the double-stranded oligonucleotide is labelled, there are the following advantages by use of the method of the present invention.

In the nick translation method of the prior art, because the position where the site of incorporated nick could not be identified, the labelling position and labelling amount could not be controlled. Accordingly, the strength of the probe differed depending on the preparation conditions, and therefore it was difficult to prepare always a probe having a constant strength.

In the case of the present invention, during probe designing, the labelled amount can be previously predicted, and the probe can be prepared while controlling it according to the purpose.

Further, it is also possible to prepare a DNA having alternately labelled regions and non-labelled regions by adding only a labelling substance during the enzyme reaction.

The oligonucleotide double strand thus prepared has the labelling substance incorporated in both the chains, each chain functioning as a probe having high specific activity.

In the primer extension method of the prior art, labels could be incorporated into those with a length of 50 base pairs or less, while in the nick translation method, into those with a length of 500 base pairs or more. In the present invention, it is also possible to prepare a probe with an intermediate length between these.

The third present invention is to provide an oligonucleotide having a fixing substance introduced therein in place of introducing the labelling substance in the step (f) or the step (9) as described above in the first and second present inventions.

More specifically, (d) two or more of single-stranded oligonucleotides having 6 bases pairs or more of complementary sequences at the 3'-ends are synthesized by a DNA synthesizer. (e) Next, these two oligonucleotides are bound at the complementary portions according to the annealing reaction to constitute partially a double strand. (g) The partial double strand formed at this time functions as the primer for the two DNA's respectively synthesized. With different nucleotides triphosphate and a nucleotide triphosphate derivative which is a fixing substance, and reagents for polymerization of the nucleotide triphosphates and nucleotide triphosphate derivative, and with the protrudent single strand portion as the template, a double strand is synthesized while synthesizing an oligonucleotide having complementary sequence in the direction from the 5'-side to the 3'-side. In the case, the fixing substance is introduced into either one or both of a pair of oligonucleotides, but an oligonucleotide with higher yield can be formed in the latter, because one having the fixing substance introduced into both can readily react with a carrier. Further, in the present invention, (h) it is also possible to separate the double-stranded oligonucleotide obtained in the step (g) into single strands. The step (g) is described in more detail.

At this time, one or more kinds of fixing substance are added.

The fixing substance as mentioned in the present invention is a nucleotide triphosphate derivative having a binding group which is bound to the nucleotide triphosphate introduced into the DNA hybrid forming body by the extension reaction by use in the polymerizing reagent in combination through the specific affinity with a carrier. Specifically, as the above-mentioned nucleotide triphosphate derivative, biotin, heavy metal derivatives, homopolynucleotides, etc. may be employed.

Also, as the enzyme to be used as the polymerizing reagent, there may be included *E. coli* DNA polymerase I, Klenow fragment of DNA polymerase, T4DNA polymerase (T. Maniatis et al, Molecular Cloning 108, Cold Spring Harbor Laboratory), T7DNA polymerase (S. Tabor et al, Proc. Natl. Acad. Sci. USA, 84, 4767–4771 (1987), thermally stable DNA polymerase (R. k. Saiki et al, Science, 239, 487–491 (1988), other available DNA polymerases, reverse transcriptases, and other enzymes, such as enzymes promoting binding of nucleotides in appropriate modes for forming the primer extension products of the respective nucleic acids which are complementary.

By forming a double-stranded oligonucleotide according to the above-described formation method, a double-stranded oligonucleotide comprising oligonucleotides with a length of 100 mer will be simply prepared.

By separating the double-stranded oligonucleotide into single strands, an oligonucleotide having a fixing substance introduced therein can be prepared. By hybridizing the oligonucleotide having the fixing substance introduced therein as the probe nucleic acid with a sample nucleic acid, through the above-mentioned fixing substance, the hybrid and the carrier are bound, whereby said hybrid forming body can be separated with good efficiency from the non-hybrid forming body.

The affinity pair portion formed between the fixing substance and the carrier as mentioned above is a component having affinity for other components. For example, there may be included antigen-antibody such as biotin-avidin or streptoavidin, hapten-antibody, flavin adenine nucleotide (FAD)-glucose oxidase, biotin-antibotin antibody, etc., heavy metal derivative-thio group and various homopolynucleotides such as polydG-polydC, polydA-polydT and polydA-polyU as such affinity pairs.

The above carrier is bound to the nucleotide triphosphate derivative as mentioned above through affinity, but not to nucleotide triphosphate, and has the property capable of separating the hybrid forming body from the non-hybrid binding body by binding to the nucleotide triphosphate derivative.

As the separation method, there are methods such as centrifugation, adsorption, etc.

To describe in more detail about separation, the separation method and a suitable kind of carrier can be selected depending on whether the procedure for binding the carrier to the fixing substance is before or after formation of the hybrid forming body. For example, after hybridization of the probe having the fixing substance introduced therein with the target nucleic acid, the above-mentioned carrier is bound to the fixing substance, and the bound product can be separated by centrifugation or by having the carrier onto the fixing substance. Alternatively, a probe already having separation function may be formed by having an insoluble carrier having the function of being separated bound to the fixing substance before hybridization, and then the probe may be hybridized with the target nucleic acid and separated by centrifugation. The carrier is selected particularly from the following substance (hereinafter called ligand) is selected. Here the ligand has the property capable of bonding to both the fixing substance and the insoluble carrier.

Examples of the ligand may include antibodies such as streptoavidin, avidin, glucose oxidase, anti-biotin antibody, etc. And, by bonding the fixing substance to the ligand, and further bonding the ligand to the insoluble carrier, a probe to be separatable is prepared.

As the organic polymer substance to be used for the insoluble carrier to be separatable by centrifugation, there can be included water-insoluble organic polymer substances obtained by polymerization of at least one of vinyl type monomers comprising aromatic vinyl compounds, esters or amides of unsaturated carboxylic acids, unsaturated nitriles, halogenated vinyl compounds, conjugated diene compounds, and lower aliphatic vinyl esters, water-insoluble polymer substances obtained by chemical modification of said organic polymer substances, or crosslinked products of polysaccharides such as agarose, dextran, cellulose, etc., and crosslinked products of methylated albumin, gelatin, collagen, casein, etc.

The oligonucleotide of the present invention can be said to be a probe for capturing prepared by a simple method.

Furthermore an oligonucleotide obtained by another method is to be described below.

For a desired nucleic base sequence, (6) a plural number of single-stranded oligonucleotides having complementary sequences of 6 base pairs or more at the 3'-end or the 5'-end are synthesized by a DNA synthesizer as shown in FIG. 1. (7) Next, phosphoric acid groups are attached to the 5'-ends of the respective oligonucleotides. (8) Next, these two oligonucleotides are bound at the complementary portions according to the annealing reaction to constitute partially a double strand. (12) One of the partial double strands formed at this time functions as the primer for the other oligonucleotide synthesized. With various different nucleotide triphosphates and a nucleotide triphosphate which is the fixing substance, and reagents for polymerization of the nucleotide triphosphates and nucleotide triphosphate derivative, and with the protrudent single strand as the template, a double strand is synthesized while synthesizing an oligonucleotide having complementary sequence in the direction from the 5'-side to the 3'-side. (10) When a nick is formed in the oligonucleotide thus prepared, ligation may be performed with an enzyme so that there may be no nick. (11) The double strand is separated to form single-stranded oligonucleotides.

The step (12) is to be described in more detail.

(12) Into the solution are added appropriate amounts of dATP, dCTP, dGTP and TTP as synthetic reagents which are nucleotide triphosphates.

At this time, one or more kinds of fixing substances is added. The fixing substance and the enzyme to be used as the polymerizing reagent are already described in the above.

When the oligonucleotide nucleic acid sequence is correlated with genetic diseases, tumor diseases or infectious diseases, it can be effectively utilized for analysis.

A feature of the fourth present invention resides in confirming that, in the respective formation method of oligonucleotides as described, more preferably, the complementary base sequence portion has 13 or more of hydrogen bonds formed between one oligonucleotide and the other oligonucleotide.

The present invention is described below in more detail by referring to Examples.

EXAMPLE 1

Two kinds of oligonucleotides as shown below each having EcoRI site at the 5'-end were synthesized by means of a DNA synthesizer (Model 381A, available from Applied Biosystems).

```
5' GCGCTAATGGGAATTCGGACGCTCTATTTC
CTCGTGAAAGGGATGGGCGTTGCGGACCCAGATGC
AAAGAAATTCTACGCCATTGCGCAG 3'
```

-continued
```
5' CTCGCCCAGGAATTCCGTTCACGATGTACC
TCTCGATGCTGCTGGGGTATGGCCTCACAATGGTAC
CGTTCGGTGGGGAGCCTGCTGCGCAA 3'
```

Eight bases from the 3'-end are complementary to each other.

For a part of these oligonucleotides synthesized, 10% polyacrylamide gel (containing 7M urea) electrophoresis was conducted for examination of its purity. As the result, the purity was found to be about 10%, and therefore each 2 $\mu$g oligonucleotide was purified according to the above electrophoresis, extracted with 1 mM EDTA to be used in the following reactions.

Each oligonucleotide in an amount of 2 $\mu$g was placed in an Eppendorf tube, 5 $\mu$l of a 10×annealing solution (100 mM Tris-HCl, pH 8.0; 60 mM, MgCl$_2$; 60 mM β-mercaptoethanol; 500 mM NaCl) was added, and the mixture was made up to 50 l with distilled water. The mixture was heated in a beaker containing hot water of 65° C. for 10 minutes, then cooled slowly to room temperature (time required was about one hour). According to this reaction, the two oligonucleotides form a partial double strand as shown below.

```
   —Non-binding ——┐┌— Binding —┐┌— Non-binding—
      portion       ║  portion   ║   Portion
   5'......CTACGCCATTGCGCAG 3'
                   | | | | | | | |
                3' AACGCGTCCGAGGGGTGGCTT 5'
```

Into 50 $\mu$l of this solution were added each 2 $\mu$l of 1 mM dATP, dGTP, TTP, and dCTP, 5 $\mu$l of 10×annealing solution, 32 $\mu$l of distilled water, and after thorough mixing, 16 units of Klenow fragment of DNA polymerase (TOYOBO) were added, followed by heating at 37° C. for one hour to perform the extension reaction.

Then, for confirming whether the double-stranded DNA has been prepared as programmed, after phenol extraction, ethanol precipitation were performed from the above reaction solution, digestion was performed with a restriction enzyme EcoRI, and the resultant fragment was inserted at the EcoRI site of a cloning vector pUC 19. When *E. coli* JM 109 was transformed with the plasmid pUC19 having the synthesis gene inserted therein, colonies bearing the plasmid containing the double-stranded gene with high efficiency ($10^6$ colonies or more per 1 $\mu$g of DNA) were obtained. In view of the fact that no ligation is effected to the EcoRI site of pUC19 when synthesis is incomplete, it can be said that the extension reaction with the enzyme has been completely performed.

From the colonies, DNA was prepared according to the quantitation method (the DNA sequence determination method with modified T7DNA polymerase: Saibo Kogaku (Cell Engineering) vol. 7, No. 9, 1988, p. 61), and the sequence was confirmed by use of DNA SEQUENCING SYSTEM (370A, ABI). As the result, it was confirmed that the double-stranded DNA was synthesized exactly as initially designed.

Next, comparison was made with the prior art examples. A DNA of 174 base pairs similar to the above desired DNA was prepared all by synthesis according to the prior art method. Four oligonucleotides having base lengths of 87, 87, 95 and 79 as shown below were synthesized.

Since the yield of each oligonucleotide was about 10%, each oligonucleotide was purified by electrophoresis, and the band corresponding to each length was cut out from the gel and the desired oligonucleotide was extracted from the band. When the extract was examined newly by gel electrophoresis, each oligonucleotide was found to contain 10% or more of an oligonucleotide having shorter length by one or more base (as the result of intermission of synthesis) mixed therein.

These four oligonucleotides were ligated, digested with a restriction enzyme EcoRI, and the fragment was inserted at the EcoRI site of a cloning vector pUC19. When *E. coli* JM109 was transformed with the plasmid pUC19 having the synthetic gene inserted therein, the transformation efficiency was found to be about $10^5$ colonies per 1 $\mu$g of DNA.

Such lowering in transformation efficiency may be considered to be due to the lowered ligation efficiency by mixing of the oligonucleotide shorter by one or more base during ligation of the two oligonucleotides (A and B or C and D) in each chain.

This Example is effective in that not only the labors for synthesis are half of the prior art example, but also such lowering in efficiency during ligation can be avoided.

EXAMPLE 2

Two kinds of oligonucleotides as shown below corresponding a part of the sequence of the plasmid pUC19 were synthesized by means of a DNA synthesizer (Model 381A, Applied Biosystems).

5'GATCGCCCTTCCCAACAGTTGCGCA 3'
5'CATTCGCCATTCAGGCTGCGCAA 3'

Eight bases from the 3'-end are complementary to each other.

For a part of these oligonucleotides synthesized, 20% polyacrylamide gel (containing 7M urea) electrophoresis was conducted for examination of its purity. As the result, the purity was found to be about 95% or more, and therefore each oligonucleotide was used in the following reactions without further purification.

Each oligonucleotide in an amount of 2 $\mu$g (about 130 pmole) was placed in an Eppendorf tube, 5 $\mu$l of a 10×annealing solution (100 mM Tris-HCl, pH 8.0; 60 mM, MgCl2; 60 mM β-mercaptoethanol; 500 mM NaCl) was added, and the mixture was made up to 50 $\mu$l with distilled water. The mixture was heated in a beaker containing hot water of 65° C. for 10 minutes, then cooled slowly to room temperature (time required was about one hour). According to this reaction, the two oligonucleotides form a partial double-strand as shown below.

Into 50 $\mu$l of this solution were added each 2 $\mu$l of 1 mM dATP, dGTP, and dCTP, 5 $\mu$l of 0.4 mM biotinylated UTP (BRL), 5 $\mu$l of 10×annealing solution, 32 $\mu$l of distilled water, and after thorough mixing, 16 units of Klenow fragment of DNA polymerase (TOYOBO) were added, followed by heating at 37° C. for one hour to perform the extension reaction.

Then, for removing the unreacted biotinylated UTP, the reaction mixture was purified by a gel filtration column (Bio-gelp2; available from Bio Rad, 0.5×5 cm). The desired labelled nucleotide was recovered in the fractions which had passed through the column substantially as such.

Each 0.5 ml of the respective fractions was collected, and each 2 μl was adsorbed on a nitrocellulose filter to perform color formation reaction of biotin according to the protocol of BRL. As the result, the second fraction formed the color strongly, whereby it was confirmed that the desired oligonucleotide was labelled with biotin.

Further, when a part of each fraction and the unreacted oligonucleotide were examined by Agarose gel electrophoresis, the oligonucleotide of the second fraction was clearly detected as one band longer than the unreacted oligonucleotide, whereby it was confirmed that the extension reaction with the enzyme was carried out completely.

When colony hybridization, Southern hybridization, and spot hybridization were performed with the use of this probe. Only the part of the pUC19 plasmid DNA formed the color clearly in all the cases.

Next, comparison was made with the prior art examples (the substitution synthetic method and the primer extension method).

A probe of 41 base pairs similar to the above desired prove was prepared according to the substitution synthetic method That is, two oligonucleotides of 40 base length were synthesized, and after purification by gel electrophoresis (yield of about 50%), formed into a double strand.

Next, the phosphoric acid at its 5'-end was removed, and in place thereof biotinylated dUTP was introduced with a polynucleokinase derived from T4 phage for labelling. The product was dissociated into single strands to be used as the probe.

Also, one of the above oligonucleotides of 41 base length and a primer of 8 base length complementary thereto at the 3'-end were synthesized and annealed, followed by the extension reaction with the Klenow fragment according to the same method as mentioned above to prepare a probe (the primer extension method).

5'GATCGCCCTTCCCAACAGTTGCGCAGCCTGAATGGCGAATG3'
                                    | | | | | | | |
                              3' CCGCTTAC5'

Figure 4A:
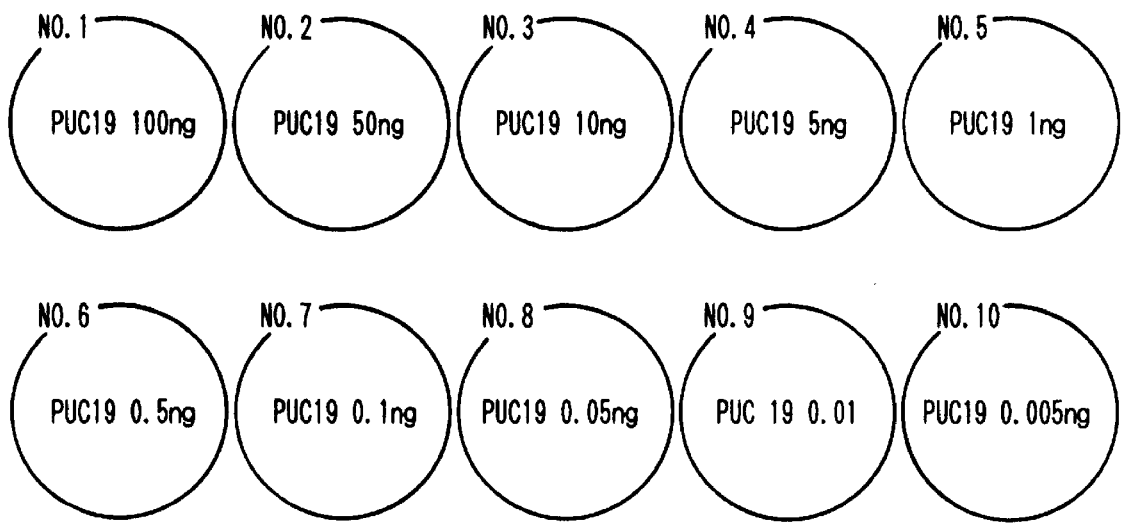
FIG. 4 is a diagram for illustration of Example 2 and Example 8.
Figure 4B:
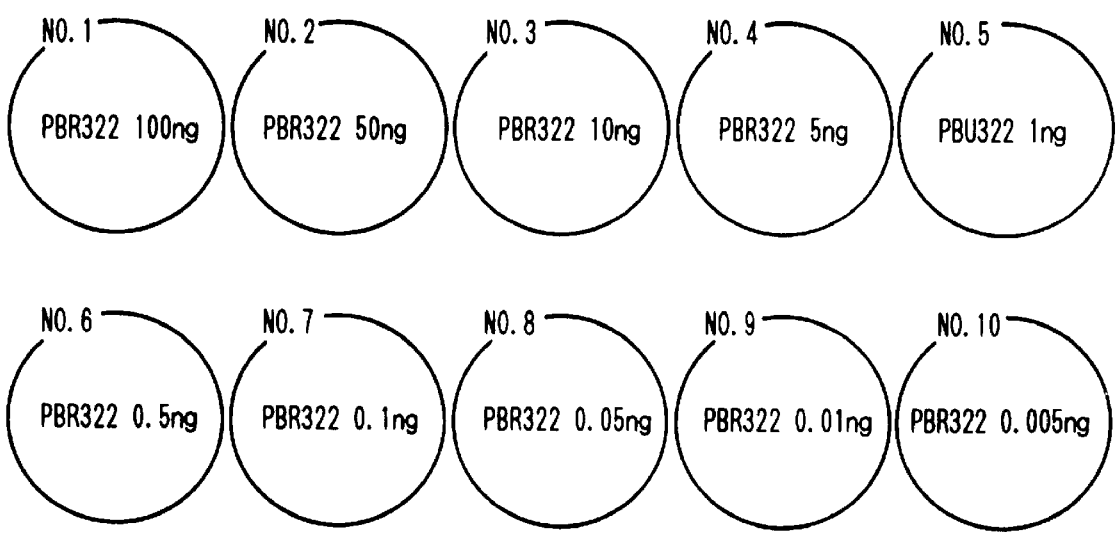

After denaturation of the plasmid DNA pUC19 and pBR322 with an alkali, DNA's in amounts of the group I No. 1 to 10, the group II No. 1 to 10 as shown in FIG. 4 was spotted on a nitrocellulose filter.

Three sheets of such filter were prepared, and after baking to 80° C. for 2 hours, hybridization reactions were carried out by use of three kinds of probes (two kinds of the prior art and the present invention in this Example 2).

When color formation reaction was carried out in conventional manner, in the probe according to the substitution synthetic method, color formation occurred under 5 ng at least in the group I, while no color formation observed in the Control of the group II. Next, in the case of using the probe according to the primer extension method, color formation occurred under up to 1 ng, and no color formation in the group II. In the probe prepared according to the method of the present invention, color formation occurred under 0.1 ng at least, but no color formation in the Control of the group II.

As the result of these experiments, it could be confirmed that not only the probe preparation is easier according to the method of the present invention than according to the prior art methods, but also the detection sensitivity is elevated by 10 to 50-fold.

EXAMPLE 3

Bacteriorhodopsin which is a protein existing in H. Halobium was purified, and the amino acid sequence from its N-end was determined up to the 16th by a protein sequencer. Based on the result, the base sequence of the DNA was estimated, and the two oligonucleotides as shown below were synthesized by means of a DNA synthesizer.

5'ATGTTGGAGTTATTGCCAACAGCAGTGG3'

5'CTGGGCCTGCGATACCCCCTCCACTGCT3'

Eight bases from the 3'-end are complementary to each other.

For a part of these oligonucleotides synthesized, 15% polyacrylamide gel (containing 7M urea) electrophoresis was conducted for examination of its purity. As the result, the purity was found to be about 90% or more, and therefore each oligonucleotide was used in the following reactions without further purification.

In an Eppendorf tube, to 45 ng (3 pmole) of each oligonucleotide was added 2 μl of a 10×annealing solution (see Example 2) and the mixture was made up to 20 μl with distilled water.

The mixture was heated in a beaker containing 200 ml of hot water of 65° C. for 10 minutes, then cooled slowly to room temperature. According to this reaction, the two oligonucleotides were annealed as shown below.

5'ATGTTGGAGTTATTGCCAACAGCAGTGG3'
                    | | | | | | | |
            3' TCGTCACCTCCCCCATAGCGTCCGGGTC5'

Next, into 20 μl of the annealed oligonucleotide solution were added 2 μl of 10×annealng solution, each 2 μl of 1 mM dATP, dCTP, and dGTP, further 100 μCi of $^{32}$P-TTP, and further after making up the total liquid amount to 40 μl with addition of distilled water, one unit of Klenow fragment of DNA polymerase was added, followed by the reaction in ice for 1 hour.

Figure 5:
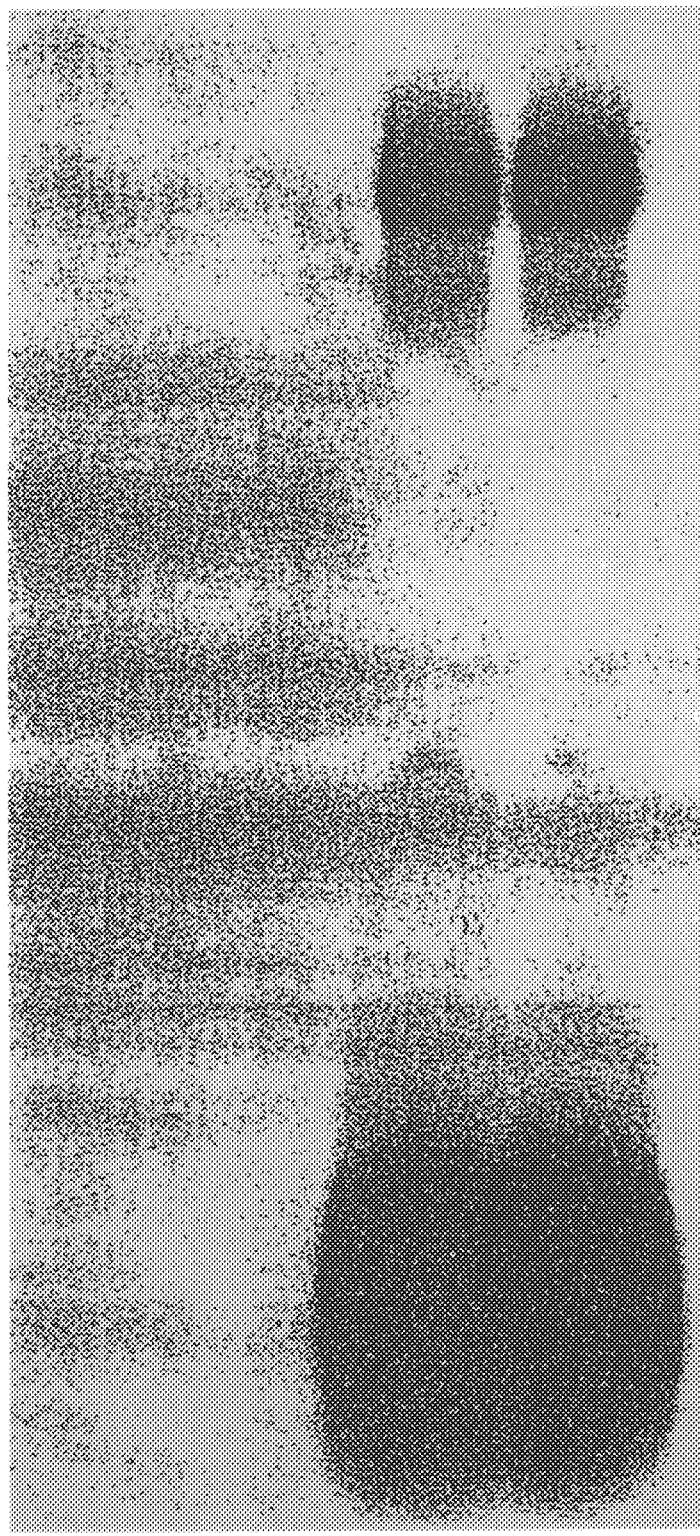
FIG. 5 is the illustration showing the results of electrophoresis for the product of Example 3.

For removing the unreacted $^{32}$P-TTP from the reaction product, 20 μl of a 98% formamide-0.05% xylene cyanol-Bromophenol Blue solution was added into the reaction solution, heated at 90° C. for 2 minutes to denature, followed by 10% polyacrylamide (containing 7M urea) gel electrophoresis. After electrophoresis at 1000 V for 3 hours, the gel was removed from the glass plate, and left to stand for about 30 seconds with a X-ray film placed thereon. When this film was developed, a band as shown in FIG. 5 drawing was obtained. As estimated from the positions electrophoresed of xylene cyanol and Bromophenol Blue, the band corresponds to 48 mer, whereby it was confirmed that the synthetic oligonucleotide of 28 mer became the 48 mer according to the extension reaction. Besides, the extension reaction had been performed completely, and the band was single without observation of by-products of shorter lengths at all.

The gel corresponding to this position was cut out, and the desired oligonucleotides were extracted overnight at 37° C. with 1 mM EDTA solution, and its intensity was measured by a liquid scintillation counter to find that the probe prepared had a very strong intensity of $10^8$ cpm or higher.

The hybridization reaction by use of this probe gave good results in all of colony, Southern and spot hybridizations.

EXAMPLE 4

When the experiment was conducted in the same manner as in Example 2 except for changing dATP, dGTP, dCTP and biotinylated UTP in Example 2 to 2 μl of 1 mM ATP, GTP and CTP and 5 μl of 0.4 mM biotinylated UTP, respectively, good results were also obtained in said Example 4.

EXAMPLE 5

The same experiment was conducted in the same manner as in Example 2 except for adding further 2 μl of 1 mM TTP upon adding dATP, dGTP, dCTP. Example 5 also exhibited good results.

EXAMPLE 6

Three oligonucleotides as shown below were synthesized by means of a DNA synthesizer (Model 381, Applied Biosystems).

1) 5'T C C G A A T T C G G T A C T G T T G C A T G T T G G A G T T A T T G C C A A C A G C A G T G G A G G G G G T A T C G C A G G C C C A G A T C A C C G G A C G T T C T G G C T A G C G C T C G G T A C G 3'

2) 5'G C G C T A A T G G G A C T C G G G A C G C T C T A T T T C C T C G T G A A A G G G A T G G G C G T C T C G G A C C C A G A T G C A A A G A A A T T C T A C G C C A T C A C G A C G G A C G T A C C G A 3'

3) 5'A T T A G C G C C T C G T C C C A G C C A T C G C G T T C A C G A T C T A C C T C T C G A T G C T G C T G G G G T A T G G C C T C A C A A T G G T A C C G T T C G T C G T A G A G T T A A A C A A C A G 3'

In the first and third synthetic oligonucleotides, the restriction enzyme EcoRI site is incorporated. Also, 8 base pairs from the 3'-end or the 5'-end (underlined portions) are complementary to each other.

A part of the oligonucleotide synthesized was examined for its purity by 10% polyacrylamide gel electrophoresis containing 7M urea to be judged as having a purity of about 10%, and therefore a band with desired length was cut out from the gel, and the desired oligonucleotides were extracted with 1 mM EDTA, recovered by ethanol precipitation and then used in the following reactions.

Each oligonucleotide in an amount of 0.1 μg was placed in an Eppendorf tube, 10 μl of 10×kinase buffer (0.5M Tris-HCl ph 8.0 ; 0.1M MgCl$_2$; 0.1M β-mercaptoethanol), 10 μl of 1 mM ATP and 1 μl of T4 polynucleotide kinase (10 units) (TOYOBO) were added, and the mixture was heated at 37° C. for one hour.

Next, 5 μl of 10×annealing solution (100 mM Tris-HCl pH 8.0 H°, 60 mM MgCl$_2$ H°, 60 mM β-mercaptoethanol H°, 500 mM NaCl) was added, and the mixture was made up to 50 μl with distilled water.

These oligonucleotides were heated in a beaker containing 200 ml of hot water of 65° C. for 10 minutes, and then left to cool slowly to room temperature. By this reaction, the three oligonucleotides were annealed as shown in FIG. 2.

Next, into 50 μl of the annealed oligonucleotide solution were added 5 μl of 10×annealing solution, each 2 μl of 1 mM dATP, dCTP, dGTP and TTP, and further distilled water to make the total liquid amount to 100 μl, and then 12 units of Klenow fragment of DNA polymerase I were added, followed by the reaction at 37° C. for one hour to perform the extension reaction.

Further, after phenol extraction were performed from the above reaction mixture, the DNA was recovered by ethanol precipitation and its length was examined by 10% polyacrylamide gel electrophoresis. As the result, a band was detected at the position of about 300 base pairs. Next, a primer of 8 base length complementary to the third synthetic oligonucleotides at the 3'-end were synthesized and annealed, followed by the extension reaction with the Klenow fragment according to the same method as mentioned above. After the DNA was recovered, digestion was performed in conventional manner with the restriction enzyme EcoRI, and the synthetic gene was ligated to the EcoRI site of the M13 phage. *E. coli* JM109 was transformed with the ligated product to obtain plaques bearing the plasmid containing the synthetic gene. When the sequence of the synthetic gene was examined in conventional manner by means of a DNA sequencing system (370A, ABI), it could be confirmed that ligation was performed in the order as initially designed.

It takes about one day for synthesis of an oligonucleotide of about 100 bases length. For preparation of the same synthetic gene as in Example 6 according to the prior art method, in addition to the three oligonucleotides of 100 bases length synthesized in Example 6, oligonucleotides of 92, 84 bases length must be synthesized. For the purpose, at least 2 superfluous days are required for synthesis. Besides, purification are also required.

According to the method of the present invention, in the case of preparing a synthetic gene of the same length as in the prior art method, it could be prepared with about half time and about half of the reagents.

EXAMPLE 7

In addition to the three oligonucleotides used in Example 6, further the three oligonucleotides shown below were synthesized, and by use of 6 oligonucleotides as the total, the same experiment as in Example 6 was conducted.

4) 5'T G A C G G T T C A T C G G T T C T A A A T T C C G T C A C G A G C G T A C C A T A C T A A T T G G A T C T A C T G G G C G C G G T A C G C T G A C T G G C T G T T C A C C A C G C C G C T G T T G T T 3'

5) 5'A A C C G T C A T C G C G T T G C G C G T T G A C G C G G A T C A G G G A A C G G T T A G A C C T C G C G T T G C T C G T T C A C G C C G A T C A G G G A A C G A T C T A C T G G G C G C G G T A C G C 3'

6) 5'T G A G A A T T C G C G A T C T T C G G C G A A G C C G A A G C G C C G G A G C T G A G C G T A C C G 3'

In the first synthetic oligonucleotide described in Example 6 and the sixth synthetic oligonucleotide, the restriction enzyme EcoRI site is incorporated. Also, 8 base pairs from the 3'-end or the 5'-end (underlined portions) are complementary to each other.

A part of the oligonucleotide synthesized was examined for its purity by 10% polyacrylamide gel electrophoresis containing 7M urea to be judged as having a purity of about 10%, and therefore a band with desired length was cut out from the gel, and the desired oligonucleotides were extracted with 1 mM EDTA, recovered by ethanol precipitation and then used in the following reactions.

Each oligonucleotide in an amount of 0.1 μg was placed in an Eppendorf tube, 10 μl of 10×kinase buffer (0.5M Tris-HCl pH 8.0; 0.1M MgCl$_2$; 0.1M β-mercaptoethanol), 10 μl of 1 mM ATP and 1 μl of T4 polynucleotide kinase (10 units) (TOYOBO) were added, and the mixture was heated at 37° C. for one hour.

Next, 5 μl of 10×annealing solution (100 mM Tris-HCl pH 8.0; 60 mM MgCl$_2$; 60 mM β-mercaptoethanol; 500 mM NaCl) was added, and the mixture was made up to 50 μl with distilled water.

These oligonucleotides were heated in a beaker containing 200 ml of hot water of 65° C. for 10 minutes, and then left to cool slowly to room temperature. By this reaction, the six oligonucleotides were annealed as shown in FIG. 3.

Next, into 50 μl of the annealed oligonucleotide solution were added 5 μl of 10×annealing solution, each 2 μl of 1 mM dATP, dCTP, dGTP and TTP, and further distilled water to make the total liquid amount to 100 μl, and then 12 units of Klenow fragment of DNA polymerase I were added, followed by the reaction at 37° C. for one hour to perform the extension reaction.

Further, phenol extraction were performed from the above reaction mixture, the DNA was recovered by ethanol precipitation and its length was examined by 10% polyacrylamide gel electrophoresis. As the result, a band was detected at the position of about 500 base pairs. Next, digestion was effected in conventional manner with the restriction enzyme EcoRI, and the synthetic gene was ligated to the EcoRI site of the M13 phage. *E. coli* JM109 was transformed with the ligated product to obtain plaques bearing the plasmid containing the synthetic gene. When the sequence of the synthetic gene was examined in conventional manner by means of a DNA sequencing system (370A, available from ABI), it could be confirmed that ligation was performed in the order as initially designed.

EXAMPLE 8

Four kinds of oligonucleotides as shown below corresponding to a part of the base sequence of the plasmid pUC19 were synthesized by means of a DNA synthesizer (Model 381A, Applied Biosystems).

5'<u>GATCGCCC</u>TTCCCAACAG<u>TTGCGCAG</u>3'
5'<u>GCCATTCG</u>CCATTCAGG<u>CTGCGCAA</u>3'
5'<u>TTTCGCCA</u>GCTGGCGTAATAG<u>CGAAGAGG</u>3'
5'<u>GGGCGATC</u>GGTGCGGG<u>CCTCTTCG</u>3'

Eight bases from the 3'-end or the 5'-end are complementary to each other.

A part of the oligonucleotide synthesized was examined for its purity by 20% polyacrylamide gel (containing 7M urea) electrophoresis. As the result, it was found to have a purity of about 95%, and therefore used without further purification in the following reactions.

Each oligonucleotide in an amount of 2 μg about 130 pmole) was placed in an Eppendorf tube, 10 μl of 10×kinase buffer (0.5M Tris-HCl pH 8.0; 0.1M MgCl$_2$; 0.1M β-mercaptoethanol), 10 μl of 1 mM ATP and 1 μl T4 polynucleotide kinase (10 units) (TOYOBO) were added, and the mixture was heated at 37° C. for one hour.

Next, 5 μl of 10×annealing solution (100 mM Tris-HCl pH 8.0; 60 mM MgCl$_2$; 60 mM β-mercaptoethanol; 500 mM NaCl) was added, and the mixture was made up to 50 μl with distilled water. This was heated in a beaker containing hot water of 65° C. for 10 minutes, and then left to cool slowly to room temperature (time required is about one hour). By this reaction, the four oligonucleotides form a partial double strand as shown below.

5'GCCATT---CTGCGCAA   GGGCGATC---CCTCTTCG3'
       ||||||||   ||||||||   ||||||||
    3'GACGCGTT---CCCGCTAG   GGAGAAGC---5'

Into 50 μl of this solution were added each 2 μl of 1 mM dATP, dGTP and dCTP, 5 μl of 0.4 mM biotinylated UTP (BRL), 5 μl of 10×annealing solution, 32 μl of distilled water, and after thorough mixing 16 units of Klenow fragment of DNA polymerase I were added, followed by the reaction at 37° C. for one hour to effect the extension reaction.

Then, for removing the unreacted biotinylated UTP, the reaction mixture was purified by a gel filtration column (Bio-gelP2; Bio Rad, 0.5×5 cm). The desired labelled nucleotide was recovered in the fractions which had passed through the column substantially as such.

Each 0.5 ml of the respective fractions was collected, and each 2 μl was adsorbed on a nitrocellulose filter to perform color formation reaction of biotin according to the protocol of BRL. As the result, the second fraction formed the color strongly, whereby it was confirmed that the desired oligonucleotide was labelled with biotin.

Next, comparison was made with the prior art examples (the substitution synthetic method, the nick translation method, and the primer extension method).

A probe with 80 base pairs similar to the above DNA was prepared according to the substitution synthetic method. That is, two oligonucleotides of 80 pairs length were prepared, and after purification by gel electrophoresis (yield of about 20%) formed into a double strand. The phosphoric acid at its 5'-end was removed, and in place thereof biotinylated dUTP was introduced with a polynucleokinase derived from T4 phage, and the labelled product obtained was dissociated into single strands to provide a probe A. Biotinylated dUTP was incorporated into the double-stranded oligonucleotide of 80 base pairs as mentioned above by nick translation to provide a probe B.

Also, by synthesizing one of the oligonucleotides of 80 bases length as mentioned above, and a primer of 8 bases length complementary thereto at the 3'-end, and after annealing them, the extension reaction with Klenow fragment was carried out in the same manner as in Example 2 to prepare a probe C (the primer extension method).

Each of the probes A, B, C was purified by gel filtration column in the same manner as mentioned above. In probe A, color formation was observed in the second fraction, but its extent was considerably pale as compared with the present invention. In probe B, substantially no color formation occurred, exhibiting that the reaction had not proceeded well. In probe C, in addition to the second fraction, color formation also occurred in the third and fourth fractions, exhibiting that considerable amounts of by-products with shorter lengths were also formed.

From these facts, it has been shown that the nick translation method and the primer extension method are unsuitable for preparation of a probe of 80 base pairs.

Next, after denaturation of the plasmid DNA pUC19 and pBR322 with an alkali, DNA's in amounts of the group I No. 1 to 10, the group II No. 1 to 10 as shown in FIG. 4 were spotted on a nitrocellulose filter.

Two sheets of such filter were prepared, and after baking to 80° C. for 2 hours, hybridization reactions were carried out by use of two kinds of probes (the substitution synthetic method which is the prior art and the present invention in this Example 8).

When color formation reaction was carried out in conventional manner, in the probe according the substitution synthetic method, color formation occurred under 5 ng at least in the group I, while no color formation observed in the Control of the group II. In the probe prepared according to the present invention, color formation occurred under 0.05 ng at least, but no color formation in the Control of the group II.

As the result of this experiment, it could be confirmed that not only the probe preparation method is easier according to the method of the present invention than according to the prior art methods, but also the detection sensitivity is elevated by 100-fold.

EXAMPLE 9

Four oligonucleotides each being a part of the DNA sequence of bacteriorhodopsin which is a protein existing in H. Halobium were synthesized by means of a DNA synthesizer.

5'GGGGTATGGCCTCACAATGGTACC3'
5'TACCCCAGCAGCATCGAGAGGTAC3'
5'TTCTGCTCCCCACCGAACGGTACC3'
5'GCAGAACCCCATCTACTGGGCGCG3'

Eight bases from the 3'-end are complementary to each other.

For a part of these oligonucleotides synthesized, 15% polyacrylamide gel (containing 7M urea) electrophoresis was conducted for examination of its purity. As the result, the purity was judged to be about 90% or more, and therefore each oligonucleotide was used in the following reactions without further purification.

In an Eppendorf tube, 45 ng of each oligonucleotide was placed, and 10 μl of 10×kinase buffer (0.5M Tris-HCl pH 8.0; 0.1M MgCl$_2$; 0.1M β-mercaptoethanol), 10 μl of 1 mATP and 1 ul (10 units) of T4 polynucleotide kinase (TOYOBO) and the mixture was heated at 37° C. for one hour.

Next, 2 μl of 10×annealing solution (see Example 8) was added and the mixture was made up to 20 ul with distilled water.

The mixture was heated in a beaker containing 200 ml of hot water of 65° C. for 10 minutes, then cooled slowly to room temperature. According to this reaction, the four oligonucleotides were annealed.

Next, into 20 μl of the annealed oligonucleotide solution were added 2 μl of 10×annealing solution, each 100 μCi of $^{32}$P-dATP, $^{32}$P-dCTP, $^{32}$P-dGTP and $^{32}$P-TTP, and further after making up the total liquid amount to 40 μl with addition of distilled water, one unit of Klenow fragment of DNA polymerase I was added, followed by heating at 37° C. for 30 minutes. For removing the unreacted $^{32}$P-TTP from the reaction product, 20 μl of a 98% formamide-0.05% xylene cyanol-Bromophenol Blue solution was added into the reaction solution, heated at 90° C. for 2 minutes to denature, followed by 10% polyacrylamide (containing 7M urea) gel electrophoresis. After electrophoresis at 1000 V for 3 hours, the gel was removed from the glass plate, and left to stand for about 30 seconds with a X-ray film placed thereon. When this film was developed, and thus a band corresponding to 78 mer was obtained. It was confirmed that the synthetic oligonucleotide of 24 mer became completely the 78 mer according to the extension reaction without observation of other products with shorter lengths. Also, it was confirmed that the extension reaction product was alternately labelled.

The gel corresponding to this position was cut out, and the desired oligonucleotides were extracted overnight at 37° C. with 1 mM EDTA solution, and its intensity was measured by a liquid scintillation counter to find that the probe prepared had a very strong intensity of $10^{10}$ cpm or higher.

The hybridization reaction by use of this probe gave good results in all of colony, Southern and spot hybridizations.

In the same manner as in Example 8, three kinds of probes of 78 mer were prepared according to the prior art methods. Then, when the unreacted radioactive substance was removed by ethanol precipitation, and the intensity of radiation of the precipitate product was measured by a scintillation counter, an intensity of $10^5$ cpm was exhibited in the probe A prepared according to the substitution synthetic method, an intensity of $10^8$ cpm was exhibited in the probe B prepared according to the primer extension method and an intensity of $10^3$ cpm was exhibited in the probe C prepared according to the nick translation method.

When these probes were examined by gel electrophoresis, although bands were observed at the portion of 78 mer in the probe A and the probe C, a number of bands of shorter by-products were observed in the probe B. Only in this case of probe B, the band corresponding to 78 mer was cut out, subjected to extraction and, ethanol precipitation to recover these probes, and the intensity of radiation was measured to be about $10^6$ cpm.

By use of these probes, for the PstI digested product of the whole DNA of H. Halobium, Southern hybridization was performed. The electrophoresis of the PstI digested product of 0.01, 0.05, 0,1, 0.5, 1 and 2 μg in each lane was conducted, after Southern blotting was performed. In the probes A and B, a weak band hybridized with a length of about 5 kb was seen in the lanes electrophorized in 2 μg and 1 μg. In the probe C, no band was observed. In the method of the present invention, a strong band was also exhibited at around 5 kb even in a lane of 0.01 μg, thus showing a detection sensitivity of 100-fold or more of the prior art method.

EXAMPLE 10

The same experiment as in Example 8 was conducted except for changing dATP, dGTP, dCTP and biotinylated UTP in Example 8 respectively to 2 μl of 1 mM ATP, GTP and CTP, and 5 μl of 0.4 mM biotinylated UTP.

The two oligonucleotide chains thus prepared had became oligonucleotides in which DNA region and RNA region were alternately incorporated in both chains.

EXAMPLE 11

The same experiment was conducted in the same manner as in Example 8 except for adding further 2 μl of 1 mM TTP upon adding dATP, dGTP, dCTP.

The Example 11 also exhibited good results.

EXAMPLE 12

(Capturing probe)

Two kinds of oligonucleotides as shown below corresponding a part of the base sequence of the plasmid pUC19 were synthesized by means of a DNA synthesizer (Model 381A, Applied Biosystems).

5'GATCGCCCTTCCCAACAGTTGCGCAG3'
5'CATTCGCCATTCAGGCTGCGCAA3'

Eight bases from the 3'-end are complementary to each other.

For a part of these oligonucleotides synthesized, 20% polyacrylamide gel (containing 7M urea) electrophoresis conducted for examination of its purity. As the result, the purity was found to be about 95% or more, and therefore each oligonucleotide was used in the following reactions without further purification.

Each oligonucleotide in an amount of 2 μg (about 130 pmole) was placed in an Eppendorf tube, 5 μl of 10×annealing solution (100 mM Tris-HCl, pH 8.0; 60 mM, MgCl$_2$; 60 mM β-mercaptoethanol; 500 mM NaCl) was added, and the mixture was made up to 50 μl with distilled water. The mixture was heated in a beaker containing hot water of 65° C. for 10 minutes, then cooled slowly to room temperature (time required was about one hour). According to this reaction, the two oligonucleotides form a partial double strand as shown below.

5'GATCGCCCTTCCCAACAGTTGCGCAG3'
3'AACGCGTCGGACTTACCGCTTAC5'

Into 50 μl of this solution were added each 2 μl of 1 mM dATP, dGTP, and dCTP, 5 μl of 0.4 mM biotinylated UTP (BRL), 5 μl of 10×annealing solution, 32 μl of distilled water, and after thorough mixing, 16 units of Klenow fragment of DNA polymerase I (TOYOBO) were added, followed by heating at 37° C. for one hour to perform the extension reaction.

Then, for removing the unreacted biotinylated UTP, the reaction mixture was purified by a gel filtration column (Bio-gelp2; Bio Rad, 0.5×5 cm). The desired labelled nucleotide was recovered in the fractions which had passed through the column substantially as such.

Each 0.5 ml of the respective fractions was collected, and each 2 μl was adsorbed on a nitrocellulose filter to perform color formation reaction of biotin according to the protocol of BRL. As the result, the second fraction formed the color strongly, whereby it was confirmed that biotin was introduced into the desired oligonucleotide.

Accordingly, this fraction was made a capturing probe solution.

(Preparation of nucleic acid for performing detection)

On the other hand, as the nucleic acids for performing detection, the three kinds of PBR322, pUC19 and a mixture thereof were prepared.

In the subsequent description, PBR322 is called Sample A, pUC19 Sample B, and the mixture of pBR 322 and pUC19 Sample C for the purpose of convenience.

Samples A, B, C were prepared according to the same procedure respectively, but in the following, description is made only about Sample A as an example. The samples were labelled.

Into a reaction mixture obtained by adding 1 μg/2 μl of a sample DNA into 2.0 μl of 10-fold TA buffer and, 16.0 μl H$_2$O, 10 units of HindIII was added, followed by complete digestion at 37° C. for 2 hours. To the product was added 2.0 units of T4 DNA polymerase, and the reaction was carried out at 22° C. for 60 minutes. To the reaction mixture were added each 3.0 μl of 2 mM dATP, dCTP and dGTP, and further 30 μCi of p32-TTP was added to carry out the reaction at 37° C. for 40 minutes. The reaction was stopped with 10 μl of 100 mM EDTA.

Each 45 μl of the above probe solution was added into each solution of A, B, C, and distilled water was added thereto to make up 150 μl.

Then, the reaction mixture was incubated at 50° C. for one hour to carry out the hybridization reaction. After the hybridization reaction, 200 μl of a 25 w/V % of a Streptoavidin-Agarose suspension at 1M NaCl, 20 mM sodium phosphate (pH 7.5) and 1 mM EDTA was added.

In a rotatory mixer, the biotinylated molecules and the Streptoavidin-Agarose were left to stand at 37° C. for 15 minutes so that they could be bound to each other. Agarose was collected by centrifugation for a short time, and the supernatant removed by aspiration. Subsequently, the Agarose was washed once in the above buffered 1M NaCl and twice in a solution containing 150 mM NaCl, 15 mM sodium citrate (pH 8) and 0.2% SDS at 37° C.

The radioactivity of the precipitate after washing was measured by a scintillation counter for several times to give the results that the biological sample containing pUC19 exhibited a value of $10^6$ to $10^7$ cpm, while the value in the sample containing only pBR322 was less than 2-fold of the background.

From the above description, it was confirmed that the capturing probe according to the present invention fully functioned.

EXAMPLE 13

Four kinds of oligonucleotides as shown below corresponding a part of the base sequence of the plasmid pUC19 were synthesized by means of a DNA synthesizer (Model 381A, Applied Biosystems).

5'GATCGCCCTTCCCAACAGTTGCGCAG3'
5'GCCATTCGCCATTCAGGCTGCGCAA3'
5'TTTCGCCAGCTGGCGTAATAGCGAAGAGG3'
5'GGGCGATCGGTGCGGGCCTCTTCG3'

In these sequences, 8 bases from the 3'-end or the 5'-end are complementary to each other.

For a part of these oligonucleotides synthesized, 20% polyacrylamide gel (containing 7M urea) electrophoresis was conducted for examination of its purity. As the result, the purity was found to be about 95% or more, and therefore each oligonucleotide was used in the following reactions without further purification.

Each oligonucleotide in an amount of 2 μg (about 130 pmole) was placed in an Eppendorf tube, 10 μl of 10×kinase buffer (0.5M Tris-HCl, pH 8.0; 0.1M, MgCl2; 0.1M β-mercaptoethanol), 10 μl of 1 mM ATP and 1 μl (10 units) of T4 polynucleotide kinase (10 units) (TOYOBO) were added, and the mixture was heated at 37° C. for one hour.

Then, 5 μl of 10×annealing solution (100 mM Tris-HCl pH 8.0; 60 mM MgCl$_2$; 60 mM β-mercaptoethanol; 500 mM NaCl) was added, and the mixture was made up to 50 μl with distilled water. The mixture was heated in a beaker containing hot water of 65° C. for 10 minutes, then cooled slowly to room temperature (time required was about one hour). According to this reaction, the four oligonucleotides formed a partial double-strand as shown below.

```
5'GCCATT---CTGCGCAA  GGGCGATC---CCTCTTCG
   ||||||||  ||||||||   ||||||||
3'G ACGCGTT---CCCGCTAG  GGAGAAGC---
```

Into 50 μl of this solution were added each 2 μl of 1 mM dATP, dGTP, and dCTP, 5 μl of 0.4 mM biotinylated UTP (BRL), 5 μl of 10×annealing solution, 32 μl of distilled water, and after thorough mixing, 16 units of Klenow fragment of DNA polymerase (TOYOBO) were added, followed by heating at 37° C. for one hour to perform the extension reaction.

Then, for removing the unreacted biotinylated UTP, the reaction mixture was purified by a gel filtration column (Bio-gelP2; Bio Rad, 0.5×5 cm). The desired labelled nucleotide was recovered in the fractions which had passed through the column substantially as such.

Each 0.5 ml of the respective fractions was collected, and each 2 μl was adsorbed on a nitrocellulose filter to perform color formation reaction of biotin according to the protocol of BRL. As the result, the second fraction formed the color strongly, whereby it was confirmed that biotin had been introduced into the desired oligonucleotide.

Accordingly, this fraction was made a capturing probe solution.

On the other hand, as the nucleic acids for performing detection, the three kinds of pBR322, pUC19 and a mixture thereof were prepared.

In the subsequent description, pBR322 is called Sample A, pUC19 Sample B, and the mixture of pBR 322 and pUC19 Sample C for the purpose of convenience.

Samples A, B, C were prepared according to the same procedure respectively, but in the following, description is made only about Sample A as an example. The samples labelled.

Into a reaction mixture obtained by adding 1 μg/2 μl of a sample DNA into 2.0 μl of 10-fold TA buffer and 16.0 μl H$_2$O, 10 units of HindIII was added, followed by complete decomposition at 37° C. for 2 hours. To the product were added 2.0 units of T4 DNA polymerase, and the reaction was carried out at 22° C. for 60 minutes. To the reaction mixture were added each 3.0 μl of 2 mM dATP, dCTP and dGTP, and further 30 μCi of p32-TTP was added to carry out the reaction at 37° C. for 40 minutes. The reaction was stopped with 10 μl of 100 mM EDTA.

Each 45 μl of the above probe solution was added into each solution of A, B, C, and distilled water was added thereto to make up 150 μl.

Then, the reaction mixture was incubated at 50° C. for one hour to carry out the hybridization reaction. After the hybridization reaction, 200 μl of a 25 w/V % of a Streptoavidin-Agarose suspension at 1M NaCl, 20 mM sodium phosphate (pH 7.5) and 1 mM EDTA was added.

In a rotatory mixer, the biotinylated molecules and the Streptoavidin-Agarose were left to stand at 37° C. for 15 minutes so that they could be bound to each other. Agarose was collected by centrifugation for a short time, and the supernatant removed by aspiration. Subsequently, the Agarose was washed once in the above buffered 1 M NaCl and twice in a solution containing 150 mM NaCl, 15 mM sodium citrate (pH 8) and 0.2% SDS at 37° C.

The radioactivity of the precipitate after washing was measured by a scintillation counter for several times to give the results that the biological sample containing pUC19 exhibited a value of $10^6$ to $10^7$ cpm, while the value in the sample containing only pBR322 was less than 2-fold of the background.

From the above description, it could be confirmed that the capturing probe according to the present invention fully functioned.

EXAMPLE 14 a. Preparation of synthetic oligonucleotide:

Four kinds of oligonucleotides as shown below containing base sequences corresponding a part of the base sequence of the plasmid pUC19 were synthesized by means of a DNA synthesizer (Model 381A, Applied Biosystems).

5'GATCGCCCTTCCCAACAGTTGCGCAG3'
5'GCCATTCGCCATTCAGGCTGCGCAA3'
5'TTTCGCCAGCTGGCGTAATAGCGAAGAGG3'
5'GGGCGATCGGTGCGGGCCTCTTCG3'

Eight bases from the 3'-end or the 5'-end are complementary to each other.

For a part of these oligonucleotides synthesized, 20% polyacrylamide gel (containing 7M urea) electrophoresis was conducted for examination of its purity. As the result, the purity was found to be about 95% or more, and therefore each oligonucleotide was used in the following reactions without further purification.

Each oligonucleotide in an amount of 2 μg (about 130 pmole) was placed in an Eppendorf tube, 10 μl of 10×kinase buffer (0.5M Tris-HCl, pH 8.0; 0.1M, MgCl$_2$; 0.1M β-mercaptoethanol), and 1 μl (10 units) of T4 polynucleotide kinase (10 units) (TOYOBO) were added, and the mixture was heated at 37° C. for one hour.

Then, 5 μl of 10×annealing solution (100 mM Tris-HCl pH 8.0; 60 mM MgCl$_2$; 60 mM β-mercaptoethanol-500 mM NaCl) was added, and the mixture was made up to 50 ul with distilled water. The mixture was heated in a beaker containing hot water of 65° C. for 10 minutes, then cooled slowly to room temperature (time required was about one hour).

According to this reaction, the four oligonucleotides form a partial double strand as shown below.

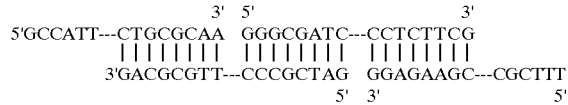

Into 50 μl of this solution were added each 2 μl of 1 mM dATP, dGTP, and dCTP, 5 μl of 0.4 mM biotinylated UTP (BRL), 5 μl of 10×annealing solution, 32 μl of distilled water, and after thorough mixing, 16 units of Klenow fragment of DNA polymerase I (TOYOBO) were added, followed by heating at 37° C. for one hour to perform the extension reaction. After the reaction, the reaction was stopped by heating at 65° C. for 5 minutes, and then deproteinization was performed by treatment with phenol.

Then, for removing the unreacted biotinylated UTP, the reaction mixture was purified by a gel filtration column (Bio-gelP2; Bio Rad, 0.5×5 cm). The desired capturing modified synthetic nucleotide was recovered in the fractions which had passed through the column substantially as such. Each 0.5 ml of the respective fractions was collected, and each 2 μl was adsorbed on a nitrocellulose filter to perform color formation reaction of biotin according to the protocol of BRL. As the result, the second fraction formed the color strongly, whereby it was confirmed that the desired double-stranded synthetic nucleotide contained biotin.

Next, the solution containing the double-stranded synthetic nucleotide as mentioned above was treated by heating at 95° C. for 5 minutes to be dissociated into single strands, to obtain a synthetic oligonucleotide.

b. Preparation of bound product of synthetic oligonucleotide and insoluble carrier:

As the insoluble carrier, gel particles with particle sizes of about 10 μm were used. The gel particles were obtained by pulverizing Agarose gel, and their surfaces were activated with cyanogen bromide and then bound to avidin. The avidin-bound gel particles were mixed with the solution containing the previous synthetic oligonucleotide for 20 minutes. At this time, the biotin incorporated within the synthetic oligonucleotide binds specifically to the avidin on the surface of gel particle.

c. Preparation of nucleic acid to be detected

As the nucleic acid to be detected, the three kinds of pUC19, pBR322 and a mixture of PUC19 and pBR322 were prepared.

Into a reaction mixture having 2 μl of 10×TA buffer, 16 μl of ddH$_2$O added into each sample of the three kinds containing 1 μg of each nucleic acid in 2 μl of distilled water were added 10 units of Hind III, followed by complete digestion at 37° C. for 2 hours. Then, phenol extraction and ethanol precipitation were performed, and the precipitate was dissolved in 10 μl of distilled water.

To the solution were added 6 μl of a mixed reagent solution (0.33M Tris-HCl pH 7,9; 33 mM MgCl$_2$, 3.3 mM dithiothreitol), 1 μl of 5 mM dCTP, 1 μl of 5 mM dGTP, 1 μl of 5 mM dATP, 1 μl of 5 mM dTTP, 1 μl of [$-^{32}$P]dGP (10 Ci), 7 μl of distilled water and 2 μl (4 units) of T4-DNA polymerase, and the reaction was carried out at 20° C. for 30 minutes to apply radioactive label. The samples were labelled.

Then, the nucleic acid to be detected of each sample applied with radioactive label was dissociated into single strands by the heat treatment at 95° C. for 5 minutes.

d. Hybridization

To the bound product of the synthetic oligonucleotide and the insoluble carrier prepared in b. were added the test sample nucleic acid solution dissociated into single strands obtained in C and 5 µl of 10×annealing solution, and the mixture was made up to 50 µl with distilled water. After the mixture was lightly stirred, it was heated in a beaker containing hot water of 65° C. for 10 minutes, and then cooled slowly for about one hour to room temperature.

After being centrifuged briefly, the supernatant was discarded, and after further washing twice with TE solution, the intensity of the precipitate was measured by a scintillation counter for several times. As the result, the sample containing pUC19 exhibited a value of $10^6$ to $10^7$ cpm, and the value in the sample containing only pBR322 was less than 2-fold of the background.

EXAMPLE 15

Preparation of synthetic oligonucleotide

Nine kinds of oligonucleotides as shown below were synthesizes by means of a DNA synthesizer (Model 381A, ABI) designed so that the double-stranded DNA of 20 mer of the final desired product may become the same sequence).

Ⓐ $^5$'T C A C A A A A A T C$^{3'}$
Ⓑ $^5$'T T G A G C G T C G A T T T$^{3'}$
Ⓒ $^5$'T C A C A A A A A T C G$^{3'}$
Ⓓ $^5$'T T G A G C G T C G A T T$^{3'}$
Ⓔ $^5$'T T G A G C G T C G A T T T T$^{3'}$
Ⓕ $^5$'T C A C A A A A A T C G A$^{3'}$
Ⓖ $^5$'T T G A G C G T C G A T T T T T$^{3'}$
Ⓗ $^5$'T C A C A A A A A T C G A C G C T C A A$^{3'}$
Ⓘ $^5$'T T G A G C G T C G A T T T T T G T G A$^{3'}$

Among them, Ⓐ and Ⓑ, Ⓒ and Ⓓ, Ⓐ and Ⓔ, Ⓓ and Ⓕ, Ⓐ and Ⓖ, Ⓒ and Ⓔ have sequences at the 3'-end complementary to each other, Ⓗ and Ⓘ have all the sequences complementary to each other.

For a part of these oligonucleotides synthesized, 20% polyacrylamide gel (containing 7M urea) electrophoresis was conducted for examination of its purity. As the result, the purity was found to be about 95% or more, and therefore each oligonucleotide was used in the following reactions without further purification.

Each oligonucleotide in an amount of 2 µg (about 130 pmole) was placed in an Eppendorf tube, 5 µl of 10×annealing solution (100 mM tris-HCl, pH 8.0; 60 mM MgCl$_2$; 60mM β-mercaptoethanol; 500 mM NaCl), and the mixture was made up to 50 µl with distilled water. Then, the mixture was heated in a beaker containing hot water of 65° C. for 10 minutes and then cooled slowly to room temperature (time required was about one hour). According to this reaction, the oligonucleotides of (1) Ⓐ and Ⓑ (2) Ⓒ and Ⓓ, (3) Ⓐ and Ⓔ, (4) Ⓓ and Ⓕ, (5) Ⓐ and Ⓖ, (6) Ⓒ and Ⓔ form partially double strands with the total hydrogen number of 11 to 16.

(1) Ⓐ and Ⓑ total hydrogen bond number at complementary portion: 11

```
5' TCACAAAAATC 3'
          |||||
       3' TTTAGCTGCGAGTT 5'
```

(2) Ⓒ and Ⓓ total hydrogen bond number at complementary portion: 12

```
5' TCACAAAAATCG 3'
          |||||
       3' TTAGCCTGCGAGTT 5'
```

(3) Ⓐ and Ⓔ total hydrogen bond number at complementary portion: 13

```
5' T C A C A A A A A T C 3'
            | | | | | |
         3' T T T T A G C T G C G A G T T 5'
```

(4) Ⓓ and Ⓕ total hydrogen bond number at complementary portion: 14

```
5' T C A C A A A A A T C G A 3'
            | | | | | |
         3' T T A G C T G C G A G T T 5'
```

(5) Ⓐ and Ⓖ total hydrogen bond number at complementary portion: 15

```
5' T C A C A A A A A T C 3'
            | | | | | | |
         3' T T T T T A G C T G C G A G T T 5'
```

(6) Ⓒ and Ⓔ total hydrogen bond number at complementary portion: 16

```
5' T C A C A A A A A T C G 3'
            | | | | | | |
         3' T T T T A G C T G C G A G T T 5'
```

On the other hand, (7) H and I, which are all complementary to each other, form the double strand as shown below:

(7) Ⓗ and Ⓘ

```
5' T C A C A A A A A T C G A C G C T C A A 3'
   | | | | | | | | | | | | | | | | | | | |
3' A G T G T T T T T A G C T G C G A G T T 5'
```

Into 50 µl of each solution of (1) to (6) were added each 2 µl of 1 mM dATP, dGTP, TTP, and dCTP, 5 µl of 10×annealing solution, 32 µl of distilled water, and after thorough mixing, 16 units of Klenow fragment of DNA polymerase I (TOYOBO) were added, followed by heating at 37° C. for one hour to carry out the extension reaction.

b. Evaluation

For confirming whether the double-stranded DNA's of (1) to (6) were prepared as intended, after phenol extraction and ethanol precipitation were conducted from the reaction mixtures of a., the precipitate was dissolved in 20 µl of H$_2$O, and the 5'-end of the double-stranded DNA of (1) to (7) was labelled with $P^3$.

Into an Eppendorf tube of 1.5 ml volume were added 20 µl of the product of the above a., 4 µl of a mixed reagent (0.5M Tris-HCl pH 7.6, 0.1M MgCl$_2$, 50 mM dithiothreitol, 1 mM spermidine), 12.5 µl of [γ-$^{32}$P] ATP (125 µCi, 3,000 Ci/mmol) and 3 µl of T4-polynucleotide kinase (12 units), and the reaction was carried out at 37° C. for 30 minutes (the total amount of the reaction mixture 39.5 µl). After the reaction, 200 µl of 2.5M ammonium acetate was added to stop the reaction.

For removing the unreacted $^{32}$P-ATP from the reaction product, 20 µl of a 98% formamide—0.05% xylenecyanol—Bromophenol Blue solution was added, and the mixture was heated at 90° C. for 2 minutes to effect modification, followed by 10% acrylamide gel (containing 7M urea)

electrophoresis. After electrophoresis at 1,000 V for 3 hours, the gel was removed from the glass plate and left to stand for about 30 seconds with an X-ray film placed thereon. When this film was developed, (5) and (6) exhibit clear bands at the same position as (7), while (3) and (4) exhibit weak bands with about 50% intensity of (7) and further with about 10% intensity for (1) and (2).

From the above results, it has been found that a double-stranded oligonucleotide which can be satisfactorily used can be formed according to the present method, when the total hydrogen bond number at the complementary sequence portion is at least 13.

c. Next, the experiments were proceeded by use of a plural number of oligonucleotides based on the results.

Four kinds of oligonucleotides as shown below were synthesized by means of a DNA synthesizer (Model 381A, Applied Biosystems).

5'A G G A A C C <u>A A G T A A</u>3'
5'<u>C T A G A C</u> A G C A G C C <u>T T A C T T</u>3'
5'<u>G T C T A G</u> T G G G C C A G <u>A T G G T A</u>3'
5'A C T G G G <u>T A C C A T</u>3'

The underlined portions at the 3'-end or the 5'-end are sequences complementary to each other.

For a part of these oligonucleotides synthesized, 20% polyacrylamide gel (containing 7M urea) electrophoresis was conducted for examination of its purity. As the result, the purity was found to be about 95% or more, and therefore each oligonucleotide was used in the following reactions without further purification.

Each oligonucleotide in an amount of 2 μg (about 130 pmole) and 5 μl of 10×annealing solution (100 mM Tris-HCl, pH 8.0; 60 mM $MgCl_2$; 60 mM β-mercaptoethanol; 500 mM NaCl) were added in an Eppendorf tube, and the mixture was made up to 50 μl with distilled water. Then, the mixture was heated in a beaker containing hot water of 65° C. for 10 minutes and then cooled slowly to room temperature (time required was about one hour).

According to this reaction, the four oligonucleotides form a partial double strand as shown below [I]:

Into 50 μl of this solution were added each 2 μl of 1 mM dATP, dGTP, TTP, and dCTP, 5 μl of 10×annealing solution, 32 μl of distilled water, and after thorough mixing, 16 units of Klenow fragment of DNA polymerase I (TOYOBO) were added, followed by heating at 37° C. for one hour to carry out the extension reaction.

For confirming whether the double-stranded DNA of [I] was prepared as programmed, after phenol extraction and ethanol precipitation were conducted from the reaction mixtures of a., the precipitate was dissolved in 20 μl of $H_2O$, and the 5'-end of the double-stranded DNA was labelled with $P^{32}$.

Into an Eppendorf tube of 1.5 ml volume were added 20 μl of the product of the above I., 4 μl of a mixed reagent (0.5M Tris-HCl pH 7.6; 0.1M $MgCl_2$; 50 mM dithiothreitol; 1 mM spermidine), 12.5 μl of [$\gamma$-$^{32}$P] ATP (125 μCi, 3,000 Ci/mmol) and 3 μl of T4-polynucleotide kinase (12 units), and the reaction was carried out at 37° C. for 30 minutes (the total amount of the reaction mixture 39.5 μl). After the reaction, 200 μl of 2.5M ammonium acetate was added to stop the reaction.

For removing the unreacted $^{32}$P-ATP from the reaction product, 20 μl of a 98% formamide—0.05% xylenecyanol—Bromophenol Blue solution was added, and the mixture was heated at 90° C. for 2 minutes to effect modification, followed by 10% acrylamide gel (containing 7M urea) electrophoresis. After electrophoresis at 1,000 V for 3 hours, the gel was removed from the glass plate and left to stand for about 30 seconds with an X-ray film placed thereon. When this film was developed, [I] exhibited a clear band with the same intensity at a position clearly longer than (7) already evaluated in the foregoing b.

EXAMPLE 16

Table 1 shows combinations of the base number at the complementary portion and its total hydrogen bond number. For A to J shown in Table 1, the base sequences at the complementary portion are selected. Then, the respective 5 sets (10 kinds) of oligonucleotides were synthesized by a DNA synthesizer (Model 381A, ABI).

These have complementary sequences to each other at the 3'-end similarly as in Example 1.

For a part of these oligonucleotides synthesized, 20% polyacrylamide gel (containing 7M urea) electrophoresis was performed for examination of its purity. As the result, the purity was found to be about 95% or more, and therefore each oligonucleotide was used in the following reactions without further purification.

Each oligonucleotide in an amount of 2 μg (about 130 pmole) and 5 μm of 10×annealing solution (100 mM Tris-HCl, pH 8.0; 60 mM $MgCl_2$; 60 mM β-mercaptoethanol; 500 mM NaCl) were added in an Eppendorf tube, and the mixture was made up to 50 μl with distilled water. Then, the mixture was heated in a beaker containing hot water of 65° C. for 10 minutes and then cooled slowly to room temperature (for about one hour).

According to this reaction, the two oligonucleotides form a partial double strand as shown below:

Into 50 μl of this solution were added each 2 μl of 1 mM dATP, dGTP, TTP, and dCTP, 5 μl of 0.4 mM biotinylated UTP (BRL), 5 μl of 10×annealing solution, 32 μl of distilled water, and after thorough mixing, 16 units of Klenow fragment of DNA polymerase I (TOYOBO) were added, followed by heating at 37° C. for one hour to carry out the extension reaction.

Then, for removing the unreacted biotinylated UTP, the reaction mixture was purified by a gel filtration column (Bio-gel P2: Bio-Rad, 0.5×5 cm). The desired labelled nucleotide was recovered almost in the fractions passed through the column as such.

Each fraction was collected each 0.5 ml, and each 2 μl was adsorbed on a nitrocellulose filter to make color formation reaction according to the protocol of BRL. As the results, the second fraction strongly color formed and then it indicates that these oligonucleotides are labelled with biotin. As shown Table 2, the inventors estimated the extent of color formation in percentage by assuming that strong coloring becomes 2, weak coloring does 1, and no coloring does zero.

From the results as described above, it has been found that an oligonucleotide can be formed by the present method provided that the total hydrogen bond number at the complementary sequence portion is a stable sequence having 13 or more.

Further, when the total hydrogen bond number at the complementary sequence portion is 13 to 15, both of those capable of forming oligonucleotides and those of forming no oligonucleotide exist depending on the base sequence of said complementary sequence portion, a number of 16 can be said to be preferable for general purpose.

TABLE 1

| Total hydrogen bond number | Base number | | | |
|---|---|---|---|---|
| | 4 | 5 | 6 | 7 |
| 12 | A | — | C | |
| 13 | | — | D | |
| 14 | | — | E | H |
| 15 | | B | F | I |
| 16 | | | G | J |

TABLE 2

| Total hydrogen bond number | Base number | | | |
|---|---|---|---|---|
| | 4 | 5 | 6 | 7 |
| 12 | 20% | — | 30% | |
| 13 | | — | 60% | |
| 14 | | — | 70% | 90% |
| 15 | | 70% | 80% | 100% |
| 16 | | — | 100% | 100% |

EXAMPLE 17

For K to R shown in Table 3, the respective three sets (6 kinds) of the oligonucleotides as shown below were synthesized by a DNA synthesizer (Model 381A, Applied Biosystems). Table 3 shows the combination of the base number and its total hydrogen bond number.

5' CTCTGACACATGCAGCTCCCGG 3'  K-1
5' GACAAGCTGTGACCGTCTCCGGG 3'

5' CTCTGACACATGCAGCTGCCCG 3'  K-2
5' GACAAGCTGTGACCGTCTCGGGC 3'

5' CTCTGACACATGCAGCTCGCCG 3'  K-3
5' GACAAGCTGTGACCGTCTCGGCG 3'

5' AAGGCCAGGAACCGTAAA 3'  L-1
5' AACGCCAGCAACGCGGCCTTTTAC 3'

5' AAGGCCAGGAACCAGTATT 3'  L-2
5' AACGCCAGCAACGCGGCCAATACT 3'

5' AAGGCCAGGAACCAAGTAA 3'  L-3
5' AACGCCAGCAACGCGGCCTTACTT 3'

5' TTAAGTTGGGTAACGCCAGGGTTTT 3'  M-1
5' TACAACGTCGTGACTGGGAAAACC 3'

5' TTAAGTTGGGTAACGCCAGATGGTA 3'  M-2
5' TACAACGTCGTGACTGGGTACCAT 3'

5' TTAAGTTGGGTAACGCCAGTCAGTT 3'  M-3
5' TACAACGTCGTGACTGGGAACTGA 3'

5' GAGAGTGCACCATATGCGGTGTGA 3'  N-1
5' CCTTACGCATCTGTGCGGTATTTCACAC 3'

5' GAGAGTGCACCATATGCGTAGCGT 3'  N-2
5' CCTTACGCATCTGTGCGGTATTACGCTA 3'

5' GAGAGTGCACCATATGCGCTAGAC 3'  N-3
5' CCTTACGCATCTGTGCGGTATTGTCTAG 3'

5' AATTCGAGCTCGGTACCCGGGGAT 3'  O-1
5' CCTGCAGGTCGACTCTAGAGGATCCCC 3'

5' AATTCGAGCTCGGTACCCGGCATC 3'  O-2
5' CCTGCAGGTCGACTCTAGAGGGATGCC 3'

5' AATTCGAGCTCGGTACCCCGTTGC 3'  O-3
5' CCTGCAGGTCGACTCTAGAGGGCAACG 3'

5' TGAGTGAGCTAACTCACATTAATT 3'  P-1
5' GGGCAGTGAGCGCAACGCAATTAAT 3'

5' TGAGTGAGCTAACTCACTATTTTT 3'  P-2
5' GGGCAGTGAGCGCAACGCAAAAATA 3'

5' TGAGTGAGCTAACTCACTATATAT 3'  P-3
5' GGGCAGTGAGCGCAACGCATATATA 3'

5' CGCCCCCCTGACGAGCATCACAAAAATC 3'  Q-1
5' TCGCCACCTCTGACTTGAGCGTCGATTTTT 3'

5' CGCCCCCCTGACGAGCATCACTATGTAT 3'  Q-2
5' TCGCCACCTCTGACTTGAGCGTCATACATA 3'

5' CGCCCCCCTGACGAGCATCACTTAACTT 3'  Q-3
5' TCGCCACCTCTGACTTGAGCGTCAAGTTAA 3'

5' ACATACGAGCCGGAAGCATAAAG 3'  R-1
5' TTAGGCACCCCAGGCTTTACACTTTATG 3'

5' ACATACGAGCCGGAAGAAGATAC 3'  R-2
5' TTAGGCACCCCAGGCTTTACAGTATCTT 3'

5' ACATACGAGCCGGAAGTGATCTT 3'  R-3
5' TTAGGCACCCCAGGCTTTACAAAGATCA 3'

In these sequences, the underlined portions are the 3'-end sequences complementary to each other.

For a part of these oligonucleotides synthesized, 20% polyacrylamide gel (containing 7M urea) electrophoresis was performed for examination of its purity. As the result, the purity was found to be about 95% or more, and therefore each oligonucleotide was used in the following reactions without further purification.

Each oligonucleotide in an amount of 2 μg (about 130 pmole) and 5 μl of 10×annealing solution (100 mM Tris- HCl, pH 8.0; 60 mM MgCl₂; 60 mM β-mercaptoethanol; 500 mM NaCl) were added in an Eppendorf tube, and the mixture was made up to 50 μl with distilled water. Then, the mixture was heated in a beaker containing hot water of 65° C. for 10 minutes and then cooled slowly to room temperature (for about one hour).

According to this reaction, the two oligonucleotides form a partial double strand as shown below:

TABLE 3

| Total hydrogen bond number | Base number | | |
|---|---|---|---|
| | 5 | 6 | 7 |
| 13 | — | L | |
| 14 | — | M | P |
| 15 | K | N | Q |
| 16 | | O | R |

TABLE 4

| Total hydrogen bond number | Base number | | | | | |
|---|---|---|---|---|---|---|
| | 5 | | 6 | | 7 | |
| 13 | — | | L-1 GTAAAA | X | | |
| | | | L-2 AGTATT | X | | |
| | | | L-3 AAGTAA | ○ | | |
| 14 | — | | M-1 GGTTTT | X | P-1 ATTAATT | ○ |
| | | | M-2 ATGGTA | ○ | P-2 TATTTTT | ○ |
| | | | M-3 TCAGTT | ○ | P-3 TATATAT | ○ |
| 15 | K-1 CCCGG | ○ | N-1 GTGTGA | X | Q-1 AAAAATC | ○ |
| | K-2 GCCCG | ○ | N-2 TAGCGT | ○ | Q-2 TATGTAT | ○ |
| | K-3 CGCCG | ○ | N-3 CTAGAC | ○ | Q-3 TTAACTT | ○ |
| 16 | | | O-1 GGGGAT | ○ | R-1 CATAAAG | ○ |
| | | | O-2 GGCATC | ○ | R-2 AAGATAC | ○ |
| | | | O-3 CGTTGC | ○ | R-3 TGATCTT | ○ |

(The mark "○" indicates those in which color formation was observed, and the mark "X" those in which no color formation was observed)

Into 50 μl of this solution were added each 2 μl of 1 mM dATP, dGTP, TTP, and dCTP, 5 μl of 0.4 mM biotinylated UTP (BRL), 5 μl of 10×annealing solution, 32 μl of distilled water, and after thorough mixing, 16 units of Klenow fragment of DNA polymerase I (TOYOBO) were added, followed by heating at 37° C. for one hour to carry out the extension reaction.

Then, for removing the unreacted biotinylated UTP, the reaction mixture was purified by a gel filtration column (Bio-gel P2: Bio-Rad, 0.5×5 cm). The desired labelled nucleotide was recovered almost in the fractions passed through the column as such.

Each fraction was collected in 0.5 ml, and each 2 μl was adsorbed on a nitrocellulose filter to effect color formation reaction according to the protocol of BRL. The results are shown in Table 4. In Table 4, the oligonucleotides marked "○", the second fraction, formed color strongly, and then these oligonucleotides could be confirmed to be labelled with biotin.

From the above results, it was understood that an oligonucleotide could be formed, provided that the sequence is such as the total hydrogen number of the complementary sequence of 13 or more.

Next, by use of a plural number of oligonucleotides, the experiments were proceeded based on these results. With reference to the base sequences of the complementary sequence portions marked "○" in Table 4, four kinds of oligonucleotides as shown below were synthesized by a DNA synthesizer (Model 381A, Applied Biosystems).

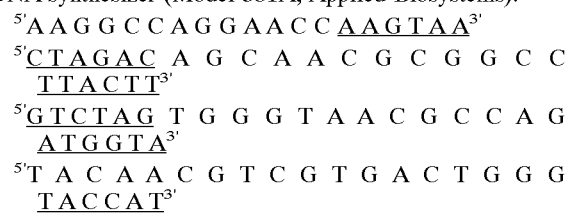

The underlined portions at the 3'-end or the 5'-end are sequences complementary to each other.

The annealing reaction was performed similarly as previously described. According to this reaction, the four oligonucleotides form a partial double strand as shown below.

Into 50 μl of this solution were added each 2 μl of 1 mM dATP, dGTP, TTP, and dCTP, 5 μl of 0.4 mM biotinylated UTP (BRL), 5 μl of 10×annealing solution, 32 μl of distilled water, and after thorough mixing, 16 units of Klenow fragment of DNA polymerase I (TOYOBO) were added, followed by heating at 37° C. for one hour to carry out the extension reaction.

Then, for removing the unreacted biotinylated UTP, the reaction mixture was purified by a gel filtration column (Bio-gel P2: Bio-Rad, 0.5×5 cm). The desired labelled nucleotide was recovered almost in the fractions passed through the column as such.

Each fraction was collected in 0.5 ml, and each 2 µl was adsorbed on a nitrocellulose filter to make color formation reaction according to the protocol of BRL. As the result, the second fraction formed color strongly, and these oligonucleotides could be confirmed to be labelled with biotin.

Further, when a part of the above color-formed fraction and a part of the color-formed fraction in the sequence B-3 were examined by Agarose electrophoresis, the above oligonucleotide was detected clearly as a single band longer (by about 2-fold) than the oligonucleotide of the sequence B-3, whereby it was confirmed that the extension reaction with the enzyme was completely carried out.

As is apparent from the above Examples, according to the first and the fourth inventions, methods with better synthesis yield, smaller by-product, and hence easier purification are obtained.

Further, a method which can synthesize a gene with a length approximate to 200 base pairs is obtained.

Further, according to the method of the present invention, since shorter oligonucleotides may be synthesized, and then procedure for purification can be omitted. Also, in the reaction of synthesis by a DNA polymerase, etc. with a single-stranded DNA as the template, it could be confirmed that the reaction could be proceeded in shorter time and more completely than in the prior art method. In a sense, this method can be also said to be a method for preparing a probe with a length which cannot be prepared by the nick translation method and the primer extension method.

Also, the labelled double-stranded oligonucleotide obtained by the present invention has a labelling substance incorporated in both chains, each chain functioning as a probe with highly specific activity, whereby efficiency of hybridization could be enhanced.

Also, according to the third invention, it has become possible to prepare a long and stable capturing probe simply.

What we claim is:

1. A method of detecting a target nucleic acid, comprising:
    (a) preparing a single-stranded probe oligonucleotide immobilized on a carrier by sequentially:
        (i) synthesizing a first and a second oligonucleotide capable of binding with each other through complementary sequences at the 3'-end regions of the first and the second oligonucleotides, and synthesizing a third and a fourth oligonucleotide, the third oligonucleotide being capable of binding with either the first or the second oligonucleotide through complementary sequences at the 5'-end regions of the first or the second oligonucleotide and the third oligonucleotide, and the fourth oligonucleotide being capable of binding with the third oligonucleotide through complementary sequences at the 3'-end regions of the third and the fourth oligonucleotides,
        (ii) binding the first, the second, the third and the fourth oligonucleotides to form a partially double-stranded oligonucleotide complex and then conducting an extension reaction in a reaction solution containing a nucleotide to which a fixing substance is bound, to polymerize nucleotides onto the 3'-end regions of the partially double-stranded oligonucleotide complex to form a double-stranded oligonucleotide in which a polymerized oligonucleotide portion of the double-stranded oligonucleotide is formed between the first and third oligonucleotide and between the second and fourth oligonucleotide, or between the first and fourth oligonucleotide and between the second and third oligonucleotide, in each of the polymerized oligonucleotide portions the fixing substance is incorporated,
        (iii) denaturing the double-stranded oligonucleotide to form a single-stranded probe oligonucleotide, and
        (iv) immobilizing the single-stranded probe oligonucleotide on the carrier by binding the fixing substance in each of the polymerized oligonucleotide portions to the carrier;
    (b) hybridizing the single-stranded probe oligonucleotide immobilized on the carrier with a target single-stranded nucleic acid labeled with a labeling substance in a mixture of different nucleic acids, to obtain a double-stranded hybrid nucleic acid containing the labeling substance;
    (c) separating the double-stranded hybrid nucleic acid from the mixture; and
    (d) detecting the labeling substance in the separated double-stranded hybrid nucleic acid.

2. The method according to claim 1, wherein the labeling substance is a radioactive labeling substance.

3. The method according to claim 1, wherein the carrier is an insoluble carrier.

4. A method of separating a target nucleic acid from a mixture of different nucleic acids, comprising:
    (a) preparing a single-stranded probe oligonucleotide immobilized on a carrier by sequentially:
        (i) synthesizing a first and a second oligonucleotide capable of binding with each other through complementary sequences at the 3'-end regions of the first and the second oligonucleotides, and synthesizing a third and a fourth oligonucleotide, the third oligonucleotide being capable of binding with either the first or the second oligonucleotide through complementary sequences at the 5'-end regions of the first or the second oligonucleotide and the third oligonucleotide, and the fourth oligonucleotide being capable of binding with the third oligonucleotide through complementary sequences at the 3'-end regions of the third and the fourth oligonucleotides,
        (ii) binding the first, the second, the third and the fourth oligonucleotides to form a partially double-stranded oligonucleotide complex and then conducting an extension reaction in a reaction solution containing a nucleotide to which a fixing substance is bound, to polymerize nucleotides onto the 3'-end regions of the partially double-stranded oligonucleotide complex to form a double-stranded oligonucleotide in which a polymerized oligonucleotide portion of the double-stranded oligonucleotide is formed between the first and third oligonucleotide and between the second and fourth oligonucleotide, or between the first and fourth oligonucleotide and between the second and third oligonucleotide, in each of the polymerized oligonucleotide portions the fixing substance is incorporated,
        (iii) denaturing the double-stranded oligonucleotide to form a single-stranded probe oligonucleotide, and
        (iv) immobilizing the single-stranded probe oligonucleotide on the carrier by binding the fixing substance in each of the polymerized oligonucleotide portions to the carrier;
    (b) hybridizing the single-stranded probe oligonucleotide immobilized on the carrier with a target single-stranded nucleic acid in the mixture of different nucleic acids, to obtain a double-stranded hybrid nucleic acid; and
    (c) separating the double-stranded hybrid nucleic acid from the mixture.

5. The method according to claim 4, wherein the carrier is an insoluble carrier.

* * * * *

UNITED STATES PATENT AND TRADEMARK OFFICE
CERTIFICATE OF CORRECTION

PATENT NO. : 5,830,643
DATED : November 3, 1998
INVENTOR(S) : NOBUKO YAMAMOTO ET AL.

It is certified that error appears in the above-indentified patent and that said Letters Patent is hereby corrected as shown below:

Title page, item [56] under Foreign Patent Documents:
Insert --0130166  1/1985  EPO--.
Insert --0316108  5/1989  EPO--.

COLUMN 2

Line 35, "an restriction" should read --a restriction--.
Line 55, "the both" should read --both--.

COLUMN 3

Line 17, "and" should be deleted.

COLUMN 5

Line 31, "at the" should read --that the--.
Line 49, "unpractically a" should read --an impracticably--.

COLUMN 6

Line 24, "oligonucleotide." should read --oligonucleotides.--.

UNITED STATES PATENT AND TRADEMARK OFFICE
CERTIFICATE OF CORRECTION

PATENT NO. : 5,830,643

DATED : November 3, 1998

INVENTOR(S): NOBUKO YAMAMOTO ET AL.

It is certified that error appears in the above-identified patent and that said Letters Patent is hereby corrected as shown below:

COLUMN 7

Line 26, "oligonucleotide," should read
      --oligonucleotides,--.

COLUMN 9

Line 29, "said the other" should read --said other--; and
      "oligonucleotide," should read --oligonucleotides,--.
    Line 67, "DNA's" should read --DNAs--.

COLUMN 10

Line 28, "Harbar" should read --Harbor--.
    Line 29, "(1987)," should read --1987)),--.
    Line 31, "(1988), should read --(1988)),--.
    Line 55, "DNA's" should read --DNAs--.

COLUMN 12

Line 46, "a tumor" should read --tumerous--.

COLUMN 13

Line 50, "Harbar" should read --Harbor--.
    Line 52, "(1987)," should read --(1987)),--.
    Line 53, "(1988)," should read --(1988)),--.
    Line 60, "at the a" should read --at a--.
    Line 62, "reagent" should read --reagents--.

UNITED STATES PATENT AND TRADEMARK OFFICE
CERTIFICATE OF CORRECTION

PATENT NO. : 5,830,643

DATED : November 3, 1998

INVENTOR(S): NOBUKO YAMAMOTO ET AL.

It is certified that error appears in the above-identified patent and that said Letters Patent is hereby corrected as shown below:

COLUMN 14

```
Line 15, "DNA's" should read --DNAs--.
Line 33, "Into" should read --Added into--; and
    "added" should be deleted.
Line 41, "to be" should be deleted.
Line 53, "(1987)," should read --(1987)),--.
Line 54, "(1988)," should read --(1988)),--.
```

COLUMN 16

```
Line 35, "DNA's" should read --DNAs--.
Line 43, "In the case," should read --In such a case,--.
```

COLUMN 17

```
Line 1, "(1987)," should read --(1987)),--.
Line 3, "(1988)," should read --(1988)),--.
Line 53, "is selected" should be deleted.
```

COLUMN 19

```
Line 42, "were" should read --was--.
```

UNITED STATES PATENT AND TRADEMARK OFFICE
CERTIFICATE OF CORRECTION

PATENT NO. : 5,830,643

DATED : November 3, 1998

INVENTOR(S) : NOBUKO YAMAMOTO ET AL.

It is certified that error appears in the above-identified patent and that said Letters Patent is hereby corrected as shown below:

COLUMN 21

Line 24, "prove" should read --proof--.
    Line 51, "DNA's" should read --DNAs--.
    Line 60, "observed" should read --was observed--.
    Line 64, "group" should read --"Control of the group"--.

COLUMN 22

Line 40, "annealng" should read --annealing--.
    Line 53, "a X-ray" should read --an X-ray--.
    Line 60, "by-product" should read --byproducts--.

COLUMN 23

Line 66, "were" should read --was--.

COLUMN 24

Line 25, "are" should read --is--.

COLUMN 25

Line 16, "were" should read --was--.
    Line 47, "about" should read --(about--.
    Line 50, "$\mu$l T4" should read --$\mu$l of T4--.

UNITED STATES PATENT AND TRADEMARK OFFICE
CERTIFICATE OF CORRECTION

PATENT NO. : 5,830,643

DATED : November 3, 1998

INVENTOR(S): NOBUKO YAMAMOTO ET AL.

It is certified that error appears in the above-identified patent and that said Letters Patent is hereby corrected as shown below:

COLUMN 26

Line 50, "DNA's" should read --DNAs--.
    Line 59, "according" should read --according to--.
    Line 61, "observed" should read --was observed--.

COLUMN 27

Line 49, "a X-ray" should read --an X-ray--.
    Line 51, "obtained. It" should read --obtained, it--.

COLUMN 28

Line 12, "and," should read --and--.
    Line 33, "became" should read --become--.
    Line 47, "sponding" should read --sponding to--
    Line 56, "conducted" should read --was conducted--.

COLUMN 29

Line 37, "and," should read --and--.

COLUMN 30

Line 6, "sponding a" should read --sponding to a--.
    Line 67, "labelled." should read --were labelled.--.

UNITED STATES PATENT AND TRADEMARK OFFICE
CERTIFICATE OF CORRECTION

PATENT NO. : 5,830,643

DATED : November 3, 1998

INVENTOR(S) : NOBUKO YAMAMOTO ET AL.

It is certified that error appears in the above-identified patent and that said Letters Patent is hereby corrected as shown below:

COLUMN 31

Line 40, "corresponding a" should read
      --corresponding to a--.

COLUMN 32

Line 28, "Next,the" should read --Next, the--.
    Line 55, "pH 7,9     should read --pH 7,9;--.

COLUMN 33

Line 21, "synthesizes" should read --synthesized--.
    Line 22, "designed" should read --(designed--.
    Line 37, "3'-end" should read --3'-ends--.

COLUMN 34

Figure (2), "3'TTAGCCTGCGAGTT5'" should read
      --3'TTAGCTGCGAGTT5'--.

Line 48, "DNA's" should read --DNAs--.
    Line 53, "$P^3$." should read --$P^{32}$.--.

COLUMN 37

Line 6, "Table" should read --in Table--.

UNITED STATES PATENT AND TRADEMARK OFFICE
CERTIFICATE OF CORRECTION

PATENT NO.  : 5,830,643

DATED       : November 3, 1998

INVENTOR(S) : NOBUKO YAMAMOTO ET AL.

It is certified that error appears in the above-identified patent and that said Letters Patent is hereby corrected as shown below:

<u>COLUMN 41</u>

Line 21, "and then" should be deleted.

Signed and Sealed this

Nineteenth Day of October, 1999

Attest:

Q. TODD DICKINSON

*Attesting Officer*         *Acting Commissioner of Patents and Trademarks*